(12) United States Patent
Akiyama

(10) Patent No.: US 7,590,279 B2
(45) Date of Patent: Sep. 15, 2009

(54) APPEARANCE INSPECTION APPARATUS FOR INSPECTING INSPECTION PIECE

(75) Inventor: Yoshihiro Akiyama, Tokyo (JP)

(73) Assignee: Saki Corporation, Tokyo (JP)

( * ) Notice: Subject to any disclaimer, the term of this patent is extended or adjusted under 35 U.S.C. 154(b) by 682 days.

(21) Appl. No.: 11/314,092

(22) Filed: Dec. 22, 2005

(65) Prior Publication Data
US 2006/0165273 A1 Jul. 27, 2006

(30) Foreign Application Priority Data

| Dec. 24, 2004 | (JP) | ............................. 2004-373750 |
| Dec. 24, 2004 | (JP) | ............................. 2004-374728 |
| Dec. 24, 2004 | (JP) | ............................. 2004-374736 |

(51) Int. Cl.
*G06K 9/00* (2006.01)

(52) U.S. Cl. .................................................. 382/147

(58) Field of Classification Search ......... 382/141–149; 348/86, 92, 125
See application file for complete search history.

(56) References Cited

U.S. PATENT DOCUMENTS

| 5,028,769 | A | * | 7/1991 | Claypool et al. ............. 235/454 |
| 6,580,502 | B1 | * | 6/2003 | Kuwabara ................. 356/237.3 |
| 6,954,268 | B2 | * | 10/2005 | Naiki et al. ............... 356/237.2 |
| 2005/0167568 | A1 | * | 8/2005 | Amar et al. ............... 250/201.2 |

FOREIGN PATENT DOCUMENTS

| CN | 2321022 | | 5/1999 |
| CN | 1517674 | | 8/2004 |
| CN | 1556920 | A | 12/2004 |
| CN | 1621818 | | 6/2005 |
| JP | SHO 63-173170 | | 7/1988 |
| JP | HEI 11-118439 | | 4/1999 |
| JP | 2001-050730 | | 2/2001 |
| JP | 2002-158500 | | 5/2002 |
| JP | 2003-099758 | | 4/2003 |

OTHER PUBLICATIONS

English Abstract of JP Application HEI 11-227,561, Publication No. 2001-050,730, Feb. 23, 2001, Patent Abstracts of Japan, Japanese Patent Office Website.
English Abstract of JP Application 2000-349,567, Publication No. 2002-158,500, May 31, 2002, Patent Abstracts of Japan, Japanese Patent Office Website.

(Continued)

*Primary Examiner*—Daniel G Mariam
(74) *Attorney, Agent, or Firm*—Neil Henderson; Ralph A. Dowell

(57) ABSTRACT

A first imaging unit and a second imaging unit of an appearance inspection apparatus for inspecting a board scan one surface of the board by being moved relative to the board. A third imaging unit and a fourth imaging unit are provided opposite to the first imaging unit and the second imaging unit, sandwiching the board, and scan the other surface of the board by being moved relative to the board. A board transport motor moves the imaging units and the board relative to each other. Each of the imaging units completes scanning the board in a single step of movement for moving the board and the scanning units relative to each other.

5 Claims, 23 Drawing Sheets

OTHER PUBLICATIONS

English Abstract of JP Application Sho 62-005,274, Publication No. 63-173,170, Jul. 16, 1988, Patent Abstracts of Japan, Japanese Patent Office Website.

English Abstract of JP Application HEI 09-278,382, Publication No. 11-118,439, Apr. 30, 1999, Patent Abstracts of Japan, Japanese Patent Office Website.

English Abstract of JP Application 2001-290,978, Publication No. 2003-099,758, Apr. 4, 2003, Patent Abstracts of Japan, Japanese Patent Office Website.

State Intellectual Property Office of People's Republic of China, The First Office Action, Mar. 14, 2008.

English Abstract of CN Application No. 02818456, Publication No. 1556920, Dec. 22, 2004, State Intellectual Property Office Of The People's Republic Of China.

English Abstract of CN Application No. 02818456, Publication No. 1556920, Dec. 22, 2004, State Intellectual Property Office Of The People's Republic Of China.

English Abstract of CN Application No. 200410002204, Publication No. 1621818, Jun. 1, 2005, State Intellectual Property Office Of The People's Republic Of China.

English Abstract of CN Application No. 97216604, Publication No. 2321022, May 26, 1999, State Intellectual Property Office Of The People's Republic Of China.

\* cited by examiner

APPEARANCE INSPECTION APPARATUS FOR INSPECTING INSPECTION PIECE

BACKGROUND OF THE INVENTION

1. Field of the Invention

The present invention relates to a technology for inspecting the appearance of an inspection piece and, more particularly, to a technology for inspecting the appearance of a package board by using multiple imaging units.

2. Description of the Related Art

Recently, electronic boards are used in a vast majority of equipment. Miniaturization, slim size and low price are persistent goals to be achieved in equipment in which electronic boards are used. For this purposes, high-integration design is practiced. Elements essential to achieve high-integration design include high-density packaging technology as well as availability of various design tools and advancement in semiconductor technology. Fabrication technology and inspection technology are important considerations to achieve high-density packaging. There is proposed a technology of using image recognition technology to inspect a printed board (hereinafter, referred to as a "board") on which components are already mounted.

For example, patent document No. 1 proposes a soldering method for a double-sided board, wherein soldering condition is monitored using images of both surfaces of a board obtained by irradiating the board with X-ray. As an another example, patent document No. 2 proposes an inspection method for a double-sided board in which a back image data is derived from a difference between front image data showing components mounted only on the front surface of the board and double-face image data showing components mounted on both surfaces of the board, and in which a determination is as to whether components are properly mounted on the front surface, by referring to a difference between the double-face image data of the board actually inspected and the back image data.

[patent document No. 1]: JP 2001-50730 A

[patent document No. 2]: JP 2002-158500 A

While technologies have been proposed for determining whether components are properly mounted on a board by referring to the images of both surfaces of the board, no technology has been proposed for efficiently imaging and analyzing both surfaces of a board on which components are mounted. With the current status of technology, an extended period of time is required if inspection depends on the recognition of a high-definition image. Further reduction in inspection time is desired.

SUMMARY OF THE INVENTION

Accordingly, a primary purpose of the present invention is to reduce inspection time required to inspect an inspection piece such as a board.

In one embodiment of the present invention, the appearance inspection apparatus which inspects an inspection piece comprises: a first scanning unit which scans one surface of the inspection piece by being moved relative to the inspection piece; a second scanning unit which is provided opposite to the first scanning unit, sandwiching the inspection piece, and which scans the other surface of the inspection piece by being moved relative to the inspection piece; and a moving unit which moves the first scanning unit, the second scanning unit and the inspection piece relative to each other. The first scanning unit and the second scanning unit complete scanning the inspection piece in a single step of movement whereby the moving unit moves the first scanning unit, the second scanning unit and the inspection piece relative to each other. According to this embodiment, scanning of both surfaces of an inspection piece is completed in a single step of movement so that inspection time is reduced. For example, the "scanning unit" may be a line sensor.

The first scanning unit and the second scanning unit of the appearance inspection apparatus according to the invention may synchronously perform each unit scanning step. According to this embodiment, it is easy to scan both surfaces of an inspection piece.

The appearance inspection apparatus may further comprise: a first illuminating unit which illuminates the inspection piece in order for the first scanning unit to scan the inspection piece; and a second illuminating unit which illuminates the inspection piece in order for the second scanning unit to scan the inspection piece. The first illuminating unit and the second illuminating unit may synchronously illuminate the inspection piece in association with each unit scanning step. According to this embodiment, illumination control for scanning an inspection piece is made easy.

The first illuminating unit and the second illuminating unit may each comprises a composite light source illuminating the inspection piece at multiple angles of incidence. The first illuminating unit and the second illuminating unit may illuminate the inspection piece at the same angle of incidence at the same time for synchronous illumination. According to this embodiment, adverse effects of optical interference on the scanning performed by a scanning unit are suppressed.

According to this embodiment, time required to inspect an inspection piece such as a board is reduced.

BRIEF DESCRIPTION OF THE DRAWINGS

Embodiments will now be described, by way of example only, with reference to the accompanying drawings which are meant to be exemplary, not limiting, and wherein like elements are numbered alike in several Figures, in which.

DETAILED DESCRIPTION OF THE INVENTION

A description will now be given of an embodiment of the present invention with reference to the attached drawings.

First Embodiment

Figure 1:
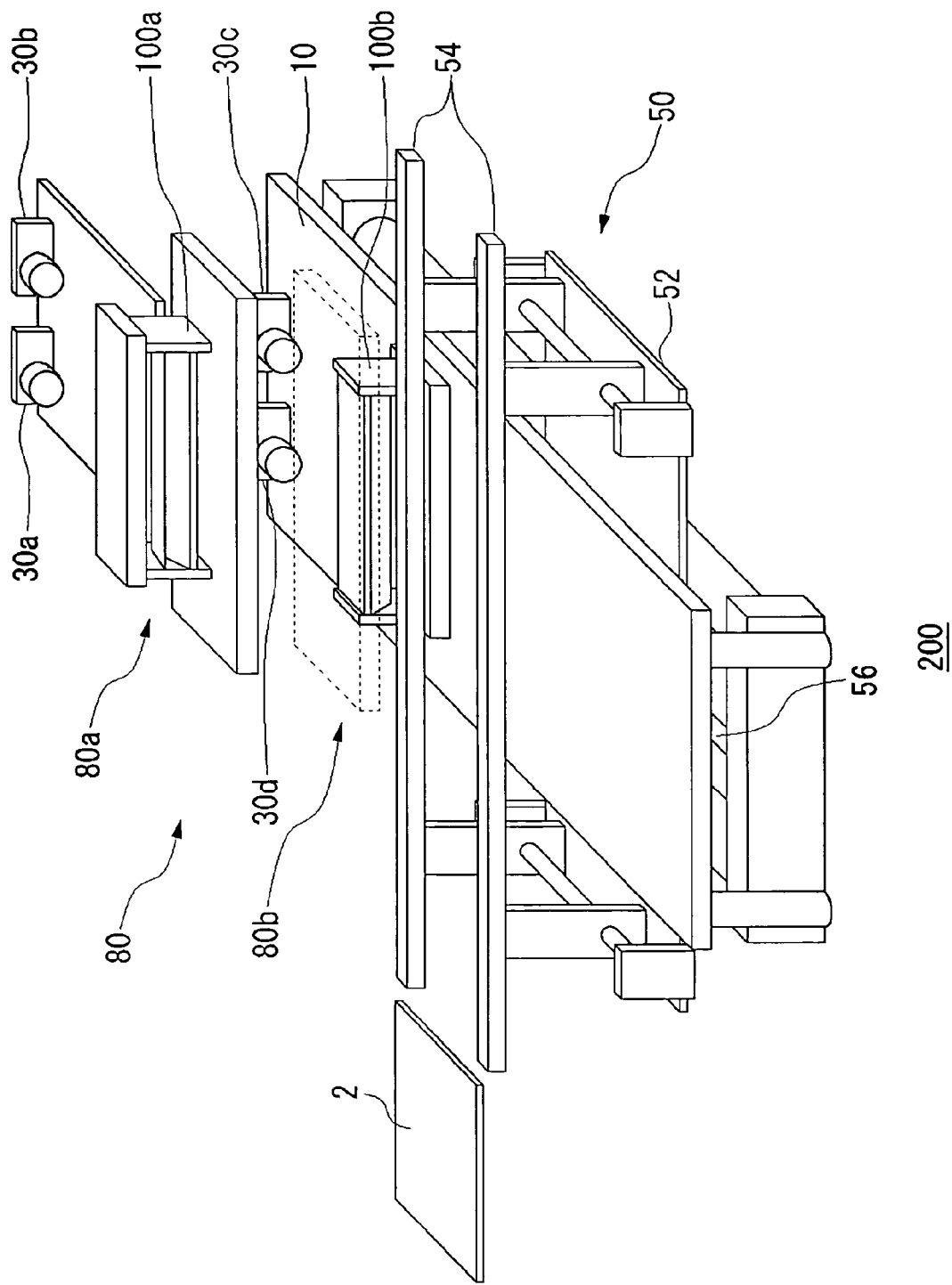
FIG. 1 shows the structure of an appearance inspection apparatus according to a first embodiment of the present invention.

FIG. 1 shows the structure of an appearance inspection apparatus 200. The appearance inspection apparatus 200 is provided with an inspection table 10, a board transport table 50 and an imaging system 80. The board transport table 50 is provided with a support plate 52, two transport rails 54 and the like. The transport rails 54 are supported by the support plate 52.

Each of the transport rails 54 is provided with a transport belt for transporting a board 2 by driving a motor. The transport rails 54 transport the board 2 mounted on the transport belts nearly to the center of the inspection table 10. A transport sensor using a noncontact sensor such as an optical sensor (not shown) for detecting the board 2 transported is provided above the transport rails 54 and practically at the center of the inspection table. When the transport sensor detects the end face of the board 2 or a detection hole provided in the board 2, it is determined that the board 2 is transported nearly to the center of the inspection table 10, whereupon the transportation of the board 2 by the transport belts is halted.

The board transport table 50 provided with the support plate 52 and the transport rails 54 is provided with an insertion unit inserted into a support shaft provided in the lower part of the appearance inspection apparatus 200. Thus, the board transport table 50 is supported so as to be movable in a direction perpendicular to the direction in which the transport rails 54 transport the board 2. By driving a ball screw 56 underneath the board transport table 50 into rotation with a motor, the board transport table 50 is moved to transport the board 2 as far as the imaging system 80. The front transport rail 54 as illustrated in FIG. 1 is provided with a clamp for correcting the configuration of the board 2 by pressing downward the board 2 mounted on the transport rail 54. The clamp corrects the deformation of the board 2 transported nearly to with the center of the inspection table 10 before the board 2 is transported as far as the imaging system 80.

The imaging system 80 is provided with an upper imaging system 80a and a lower imaging system 80b. The upper imaging system 80a comprises an upper illuminating unit 100a, a first imaging unit 30a, a second imaging unit 30b and the like. The lower imaging system 80b comprises a lower illuminating unit 100b, a third imaging unit 30c, a fourth imaging unit 30d and the like. (Hereinafter, the upper illuminating unit 100a and the lower illuminating unit 100b will generically be referred to as illuminating units 100. The first imaging unit 30a, the second imaging unit 30b, the third imaging unit 30c and the fourth imaging unit 30d will generically be referred to as imaging units 30).

When the board 2 is transported by the board transport table 50 as far as the imaging system 80, the board 2 is illuminated by the illuminating units 100 so that the imaging units 30 capture images of the surfaces of the board 2. The upper imaging system 80a is provided above the transport rails 54. The lower imaging system 80b is provided below the transport rails 54 so as to sandwich the board 2 (inspection piece) with the upper imaging system 80a. The transportation of the board 2 between the upper imaging system 80a and the lower imaging system 80b is controlled in coordination with the illumination of the board 2 by the illuminating units 100 and the imaging of the surfaces of the board 2 by the imaging units 30. This allows an image to be captured of the board 2 as the board 2 is transported by the board transport table 50 between the upper imaging system 80a and the lower imaging system 80b. The upper imaging system 80a can complete a process of capturing an image of one surface of the board 2 and the lower imaging system 80b can complete a process of capturing an image of the other surface of the board 2 in a single board transportation process. The term "single transportation process" may refer to a process whereby the board is moved in one direction only or a process whereby the board reciprocates.

When the imaging system 80 finishes capturing images of the surfaces of the board 2, the ball screw 56 is rotated so that the board transport table 50 is moved to a position that occurred when the transportation of the board 2 by the transport rails 54 is halted, whereupon the board 2 inspected is transported to a subsequent process. If another board 2 needs inspection, the board 2 is transported as described above by the transport rails 54 nearly to the center of the inspection table 10 so that images are captured of the board 2.

Figure 2:
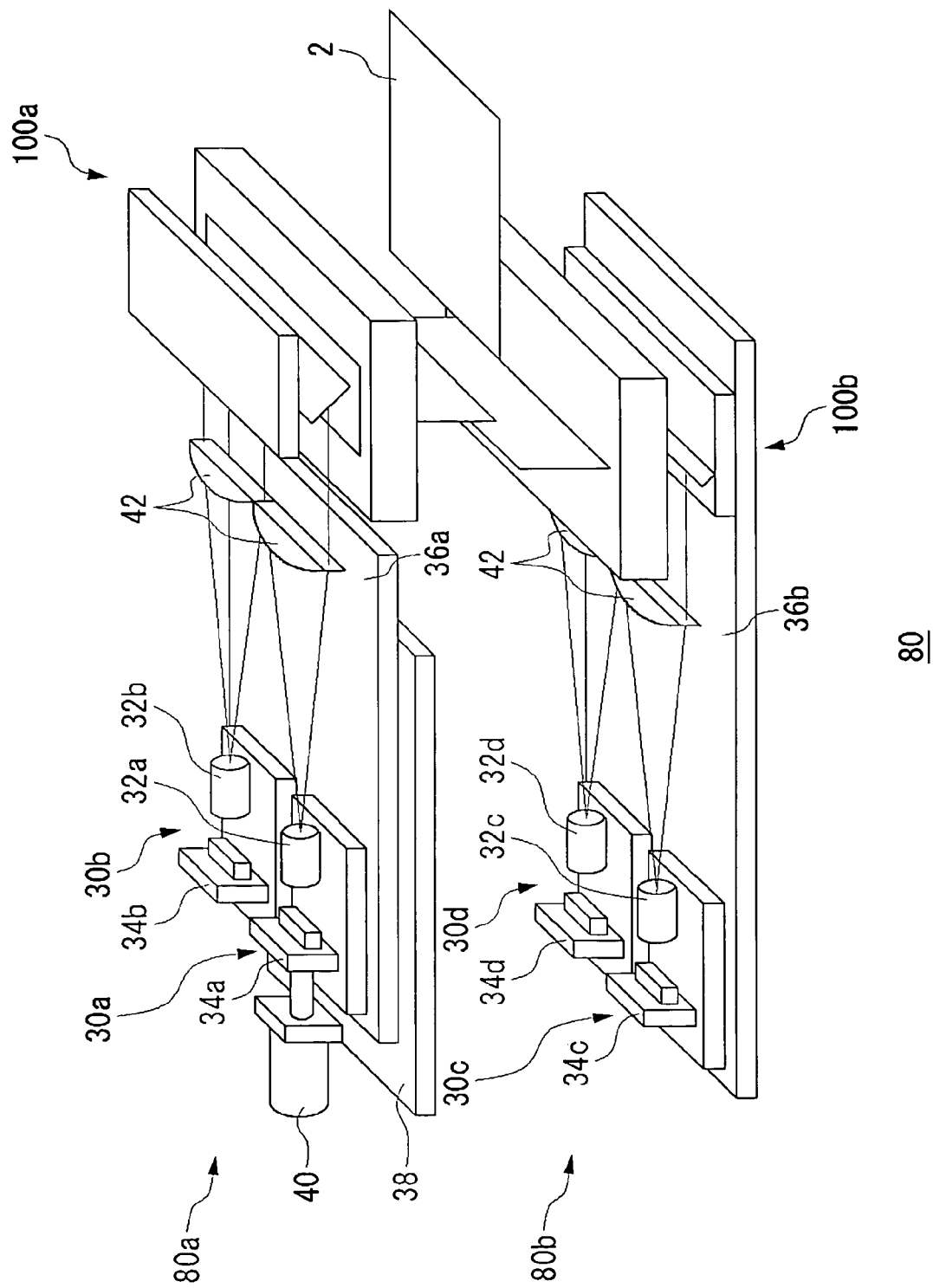
FIG. 2 shows the structure of an imaging system according to the first embodiment.

FIG. 2 shows the structure of the imaging system 80 according to the first embodiment. In the embodiment, the inspected surface of the board 2 is scanned by a line sensor so as to form an image. A determination is then made as to whether components are mounted properly by image recognition. By feeding a control signal to the motor so as to move the board transport table 50 and transport the board 2 in a direction perpendicular to the direction of scan by the line sensors, line-by-line images are obtained successively, allowing scanning to be completed in one-dimensional movement of the board 2. In some related-art appearance inspection apparatuses, the inspected surface is made to travel in two dimensions and is then halted, which steps are repeated for successive spot images to be taken. Such an approach generally requires a complex mechanism and a long period of time for inspection. In this respect, the use of a line sensor as proposed in this embodiment is advantageous.

The upper imaging system 80 comprises an upper illuminating unit 100a, an upper frame 36a, an upper support frame 38, a first imaging unit 30a, a second imaging unit 30b, a motor 40, an intermediate lens 42 and the like. The lower imaging system 80b comprises a lower illuminating unit 100b, a lower frame 36b, a third imaging unit 30c, a fourth imaging unit 30d, an intermediate lens 42 and the like.

The first imaging lens 30a, the second imaging unit 30b and the intermediate lens 42 are permanently mounted on the upper frame 36a. The first imaging unit 30a comprises a first lens 32a and a first line sensor 34a. The second imaging unit 30b comprises a second lens 32b and a second line sensor 34b. By providing multiple imaging units 30 to capture an image of one surface of the board, an image of the board 2 can be captured with a high resolution. Therefore, inspection precision is improved. Inspection speed is also improved since a captured image is subject to distributed image processing.

The upper frame 36a is supported by the upper support frame 38 so as to be slidable in a direction in which the board 2 is transported. The upper frame 36a is driven by the motor 40 to slide with respect to the upper support frame 38. An imaging control unit for controlling imaging of the board feeds a control signal to the motor 40 in accordance with preset data on the thickness of the board, so as to slide the upper frame 36a with respect to the upper support frame 38. In this way, the top surface of the board 2 is focused to capture an image of it.

In the imaging system 80a, the first imaging unit 30a and the second imaging unit 30b are provided side by side and opposite to one surface of the board 2 in order to share the task of imaging the surface of the board 2. Arrangement of the first lens 32a, the first line sensor 34a, the second lens 32b, the second line sensor 34b and the intermediate lens 42 is determined such that the imaging ranges of the first imaging unit 30a and the second imaging unit 30b overlap to ensure that components on the board 2 located between the ranges are inspected. Similarly, the third imaging unit 30c and the fourth imaging unit 30d in the lower imaging system 80b are provided side by side and opposite to the other surface of the board 2 so as to capture an image of the other surface of the board 2. Arrangement of the third lens 32c, the third line sensor 34c, the fourth lens 32d, the fourth line sensor 34d and the intermediate lens 42 is determined such that the imaging ranges of the third imaging unit 30c and the fourth imaging unit 30d overlap. A pair comprising the first imaging unit 30a and the second imaging unit 30b and a pair comprising the third imaging unit 30c and the fourth imaging unit 30d are provided to sandwich the board 2 so that an image is captured of both surfaces of the board 2 in a single step of relative movement occurring between the imaging units and the substrate 2.

To suppress blooming due to mutual optical interference, the upper illuminating unit 100a is provided toward the upstream in the direction in which the board is transported with respect to the lower illuminating unit 100b. Therefore, the board 2 transported by the board transport table 50 is moved to a start position within the scanning range of the first line sensor 34a and the second line sensor 34b. Subsequently, as the line sensors 34 (generic reference to the line sensor 34a and the line sensor 34b) finish scanning one line on the board 2, a control signal is supplied to the motor driving the ball screw 56 so as to advance the board 2 by one line. By allowing the line sensors 34 to scan the entire length of the board 2 in the direction in which the board 2 is transported, imaging of both surfaces of the board 2 is completed in a single board transportation process.

Figure 3:
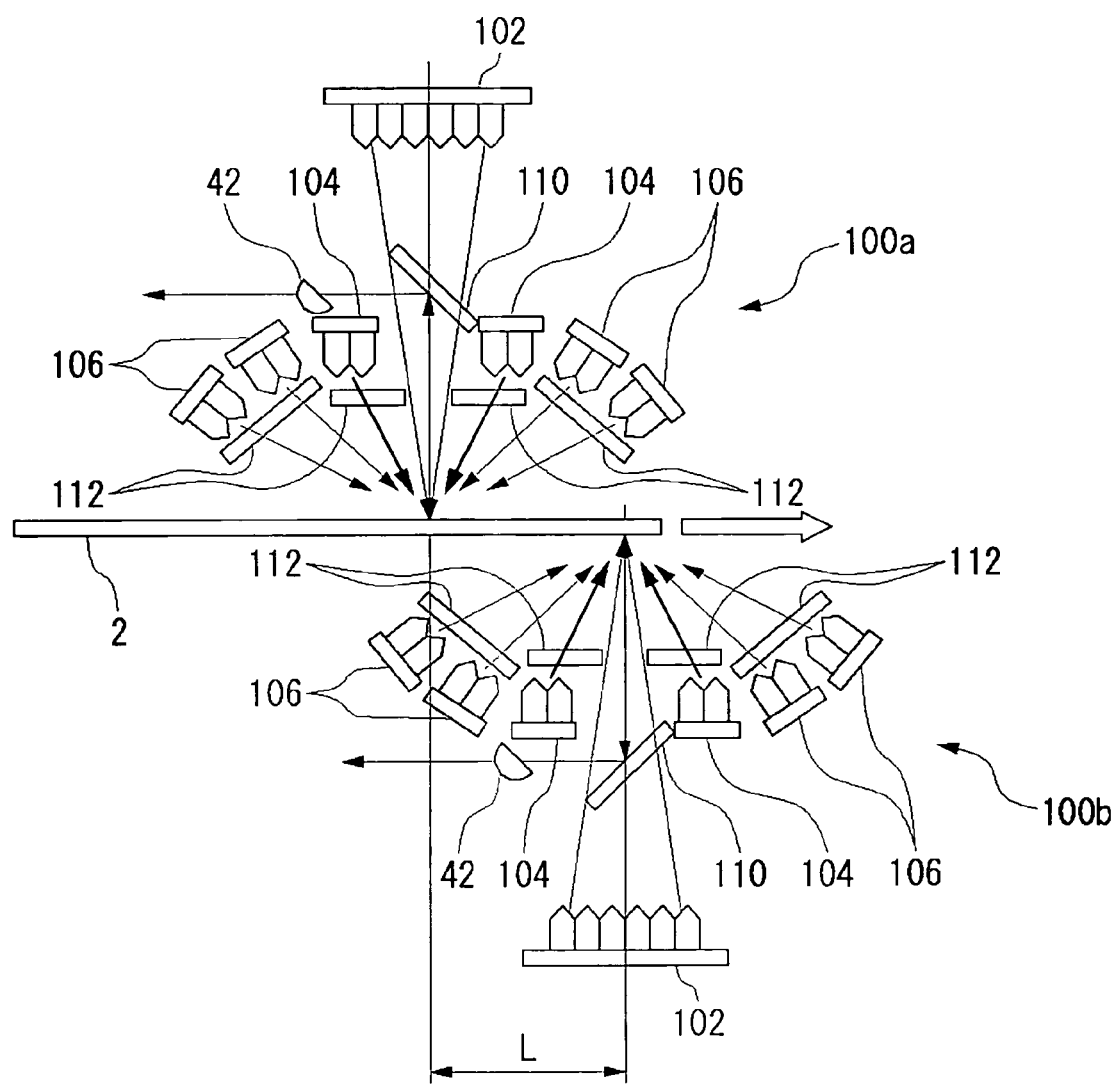
FIG. 3 shows the structure of an illuminating unit according to the first embodiment.

FIG. 3 shows the structure of the illuminating units 100 according to the first embodiment. The illuminating units 100 comprise the upper illuminating unit 100a and the lower illuminating unit 100b. Each of the upper illuminating unit 100a and the lower illuminating unit 100b comprises a first light source 102, a second light source 104, a third light source 106, a half mirror 110, an acrylic sheet 112 and the like. The first light source 102, the second light source 104 and the third light source 106 are arranged to surround the half mirror 110.

The first light source 102 comprises a group of light emitting diodes (LED) arranged in the scanning direction of the line sensors 34 so as to extend longer than the length of the board 2. The first light source 102 is provided immediately above a scan line on the board 2 scanned by the line sensors 34 for incident illumination of the board 2 below. In this embodiment, the first light source 102 comprises a group of LEDs provided on a board parallel to the board 2. For efficient incident illumination of a scanned line for inspection, the board populated with the LED group may be divided in the middle into two sub-boards each of which carries a group of LEDs arranged in the scanning direction. By using the first light source 102 for incident illumination of the board 2 and detecting the light by the line sensors 34, displacement of components, missing components and solder wetting characteristics on the board 2 can be determined.

The second light source 104 comprises a group of LEDs provided on two separate boards provided parallel to the board 2 and arranged in the scanning direction of the line sensors 34 so as to extend longer than the length of the board 2. The two boards populated with the LEDs are provided to sandwich a scanned line in the direction in which the board is transported so as not to interfere with incident illumination of the scanned line by the first light source.

Similarly to the second light source 104, the third light source 106 also comprises a group of LEDs provided on two separate boards provided parallel to the board 2 and arranged in the scanning direction of the line sensors 34 so as to extend longer than the length of the board 2. The two boards populated with LEDs are provided to sandwich a scanned line in the direction in which the board is transported so as not to interfere with the illumination of the scanned line by the first light source and the second light source. By using the second light source 104 for edge illumination of the board 2 and detecting the light by the line sensors 34, occurrence of solder bridges, wrongly mounted components, reversal in polarity can be determined.

The first light source 102 emits green light, the second light source 104 emits white light and the third light source 106 emits blue light. The light sources illuminate the board 2 at different angles of incidence. Thus, the illuminating units 100 function as a composite light source illuminating the board 2 at multiple angles of incidence. The first light source 102 is designed to emit green light and the third light source 106 is designed to emit blue light because, due to progress in the LED technology in recent years, a green LED and a blue LED are brighter than a white LED and provide a clear image with a high S/N ratio. Since a majority of printed boards are green in color, the first light source is designed to emit green light for bright incident illumination on the plane. Characters printed by laser on the body of an IC or a chip are easily recognizable by illuminating them with blue light at a low angle. Therefore, the third light source 106 is designed to emit blue light.

The angle of incidence of light emitted by the first light source 102 and incident on the inspected surface of the board 2 via the half mirror 110 is substantially zero. In this embodiment, the first light source 102 is designed to provide a certain beam width, ensuring that some light components are incident on the board 2 at an angle of incidence of zero, even if the board 2 is warped. Light reflected from a scanned line is reflected by the half mirror 110 and is transmitted through the intermediate lens 42 before being incident on the lens 32.

The acrylic sheet 112 is provided between the second light source 104 and a scanned line and between the third light source 106 and the scanned line. The acrylic sheet 112 diffuses light from the second light source 104 and the third light source 106. Since each of the second light source 104 and the third light source 106 comprises a set of LEDs as point light sources, a spot light may present itself a reflected image without the diffusive action and may adversely affect inspection precision.

In this embodiment, the second light source 104 emitting while light, the first light source 102 emitting green light and the third light source 106 emitting blue light are driven independently in the stated order so as to illuminate a scanned line three times. In each illumination, the line sensors 34 scan the board 2. In this way, images of the board 2 illuminated by the light sources are obtained.

Light from one of the illuminating units 100 may leak at an end of the board 2 to the other of the illuminating units 100. There may be holes provided in the board 2 or holes may remain unfilled with solder. Light may also leak through these holes to the other of the illuminating units 100. In case light leaked to the other of the illuminating units 100 is directly scanned by the line sensors 34, a phenomenon called blooming occurs, which may adversely affect imaging of the board 2. Therefore, the upper illuminating unit 100a and the lower illuminating unit 100b in this embodiment are provided with an offset of L with respect to each other in the direction in which the board is transported. The offset L may preferably be 50 mm or longer in respect of suppression of blooming.

Figure 4:
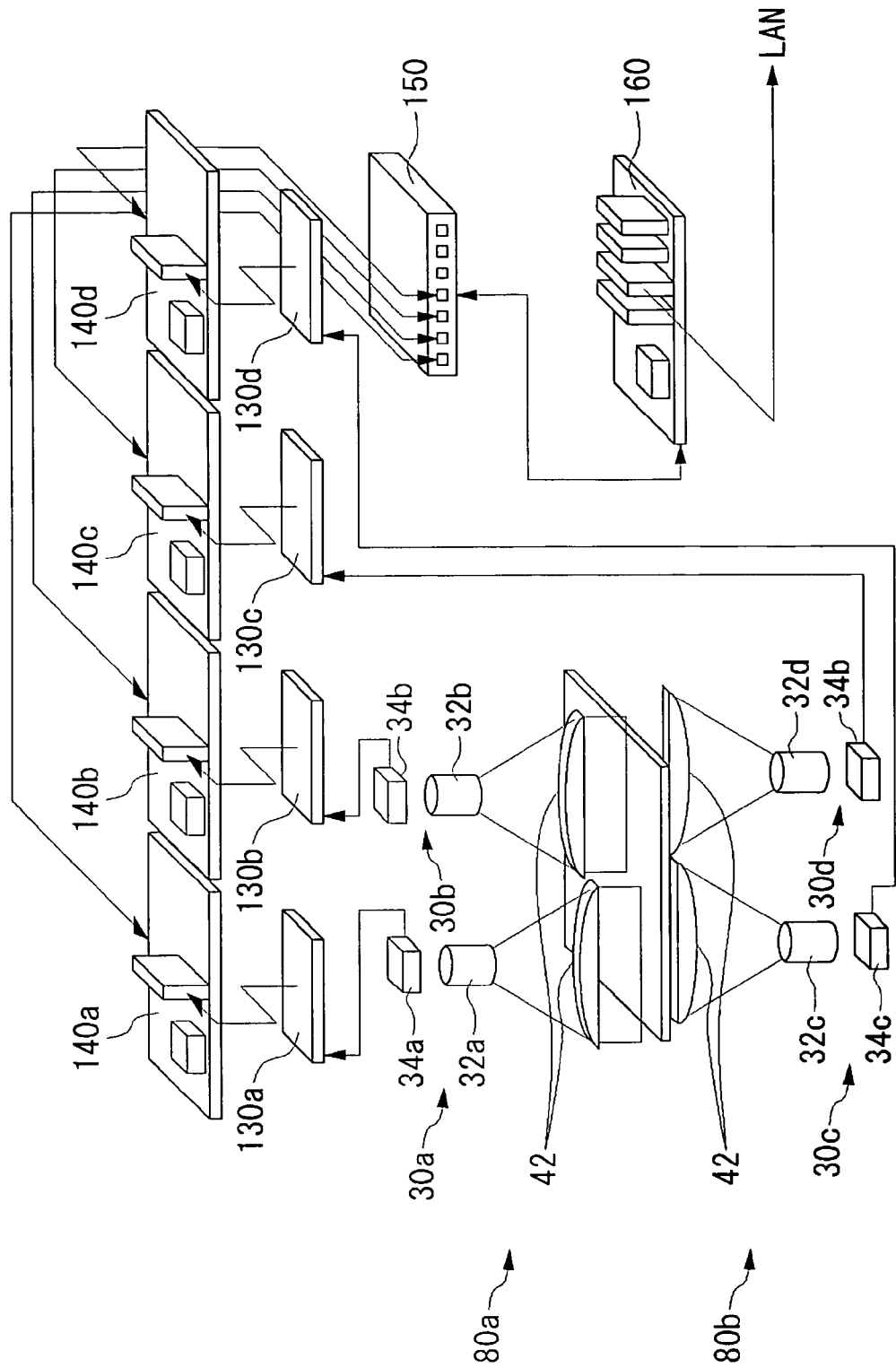
FIG. 4 shows the structure of an appearance inspection apparatus according to the first embodiment in which slave personal computers as inspecting units are included.

FIG. 4 shows the structure of an appearance inspection apparatus 200 according to the first embodiment in which slave personal computers 140 as inspecting units are included. The upper imaging system 80a comprises the first imaging unit 30a and the second imaging unit 30b. The first imaging unit 30a corresponds to a first image processing unit 130a and a first slave personal computer (PC) 140a (inspecting unit). The second imaging unit 30b corresponds to a second image processing unit 130b and a second slave PC 140b. Similarly, the lower imaging system 80b comprises the third imaging unit 30c and the fourth imaging unit 30d. The third imaging unit 30c corresponds to a third image processing unit 130c and a third slave PC 140c. The fourth imaging unit 30d corresponds to a fourth image processing unit 130d and a fourth slave PC 140d (hereinafter, the first image processing unit 130a, the second image processing unit 130b, the third image processing unit 130c and the fourth image processing unit 130d will generically be referred to as image processing units 130. The first slave PC 140l, the second slave PC 140b, the third slave PC 140c and the fourth slave PC 140d will generically be referred to as slave PCs 140).

Each of the slave PCs 140 is connected to the other slave PCs 140 via a switching hub 150 so that data transmission and reception over a network is enabled. The slave PCs 140 are also connected to a master PC 160 as a managing unit. The master PC 160 is also connected to a local area network (LAN) and is capable of transmitting results of inspection to the other PCs connected to the LAN.

Images obtained as a result of the scanning by the line sensors 34 of the imaging units 30 are transmitted to the image processing units 130 respectively corresponding to the imaging units 30. The image processing units 130 process the transmitted images and feed processed images to the respective slave PCs 140.

Each of the slave PCs 140 is provided with an image input board for receiving an image, a memory for storing image data and the like, a central processing unit (CPU) for inspecting the appearance of the board 2 by image recognition, and the like. Each of the image processing units 130 feeds an image to the corresponding image input board. Each of the slave PCs 140 supplied with the image stores the image in the memory and analyzes the image so as to acquire data for sharing including identification mark, bar code and other data that are necessary for inspection. Each of the slave PCs 140 acquiring the data for sharing transmits the data for sharing to the other slave PCs 140. The slave PCs receiving the data for sharing refer to the data for sharing so as to inspect the board 2. Thus, the slave PCs are capable of inspecting the board on their own.

The process described above is analogous to the workings of a cell inside a living organism. The cells have identical genes and select only those instructions related to them for execution, in accordance with a trigger. Analogy can be drawn between the genes and inspection according to this embodiment and between the cells and the slave PCs 140. In the related art, the master PC 160 is solely responsible for assigning inspection locations and inspection menus to multiple image processing boards. By allowing the slave PCs 140 to share the same inspection data and to select only those data portions related to them for execution, inspection precision is improved and inspection time is reduced.

Figure 5:
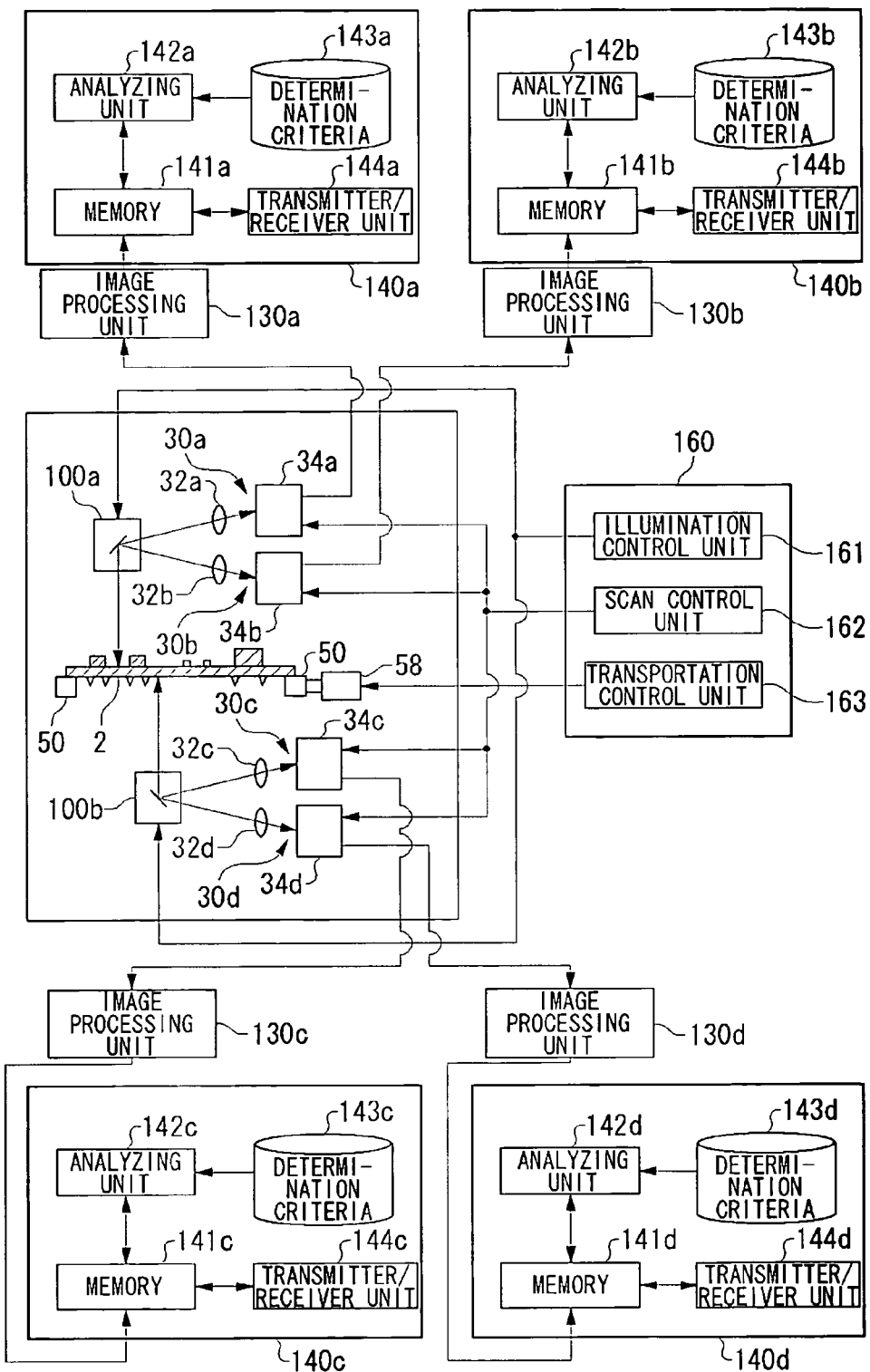
FIG. 5 is a schematic view showing the structure of an appearance inspection apparatus according to the first embodiment.

FIG. 5 is a schematic view showing the structure of an appearance inspection apparatus according to the first embodiment. The first imaging unit 30a and the second imaging unit 30b are scanning units comprising respective line sensors 34. By repeating an operation whereby the imaging units 30 scan the board 2, move the board 2 by one line and then scan again, scanning of one surface of the board 2 is completed. The third imaging unit 30c and the fourth imaging unit 30d, which are provided opposite to the first imaging unit 30a and the second imaging unit 30b and sandwich the board 2 with the first imaging unit 30a and the second imaging unit 30b, are also scanning units comprising respective line sensors 34. By repeating an operation whereby the imaging units 30 scan the board 2, move the board 2 by one line and then scan again, scanning of the other surface of the board 2 is completed.

The first imaging unit 30a, the second imaging unit 30b, the third imaging unit 30c and the fourth imaging unit 30d are provided with the first line sensor 34a, the second line sensor 34b, the third line sensor 34c and the fourth line sensor 34d, respectively. Scanning of the board 2 by the line sensors 34 is controlled by a scan control unit 162 of the master PC 160.

The board 2 is illuminated by the illuminating units 100. The line sensors 34 scans the board 2 in the illuminated stated. The illuminating units 100 comprise the upper illuminating unit 100*a* and the lower illuminating unit 100*b*. Each of the illuminating units 100 is controlled by an illumination control unit 161 of the master PC 160.

When scanning of one line is completed, the board transport table 50 is driven by a board transport motor 58 so as to move the board 2 by one line. The driving by the board transport motor 58 is controlled by a transport control unit 163 of the master PC 160.

The first line sensor 34*a*, the second line sensor 34*b*, the third line sensor 34*c* and the fourth line sensor 34*d* are controlled by the scan control unit 162 to synchronously scan the board 2 in each unit scanning step. In this way, scanning by the line sensors 34 is performed in one sitting. The transport control unit 163 moves the board 2 while the line sensors 34 are not scanning the board 2. Thereby, the board 2 is scanned efficiently and inspection time is reduced. A unit scanning step is a unit step of scanning operation each of the line sensors 34 is capable of performing. For example, a unit scanning step refers to a one-way scan from one end of the board to the other or a two-way scan.

The upper illuminating unit 100*a* and the lower illuminating unit 100*b* are controlled by the illumination control unit 161 for synchronous illumination associated with each unit scanning step. In this way, illumination control for scanning the board 2 is made easy. The scan control unit 162 controls the line sensors 34 to scan the board 2 synchronously when the illuminating units 100 are illuminating the board 2.

The upper illuminating unit 100*a* and the lower illuminating unit 100*b* are controlled by the illumination control unit 161 for synchronous illumination of the board 2 such that the units illuminate the board 2 simultaneously with light of the same color. In this embodiment, the upper illuminating unit 100*a* and the lower illuminating unit 100*b* simultaneously illuminate the board 2 with light of the same color at the same angle of incidence, the second light source 104 emitting while light, the first light source 102 emitting green light and the third light source 106 emitting blue light being driven in the stated order. Therefore, even if light from the upper illuminating unit 100*a* illuminates the surface of the board 2 to be illuminated by the lower illuminating unit 100*b*, as a result of a peripheral component presenting itself as a reflected image, adverse effects of optical interference on appearance inspection of the board 2 are minimized. The scan control unit 162 controls the line sensors 34 to synchronously run a unit scanning step when the upper illuminating unit 100*a* and the lower illuminating unit 100*b* simultaneously illuminate the board 2 with light of an angle of incidence of the second light source 104, to synchronously run a unit scanning step when the board 2 is simultaneously illuminated with light of an angle of incidence of the first light source, and to synchronously run a unit scanning step when the board 2 is simultaneously illuminated with light of an angle of incidence of the third light source.

When the board 2 is illuminated by the upper illuminating unit 100*a* and the lower illuminating unit 100*b*, the first line sensor 34*a* of the first imaging unit 30*a* scans the board 2 through the first lens 32*a*. The second line sensor 34*b* of the second imaging unit 30*b* scans through the second lens 32*b*. When the board 2 is illuminated by the lower illuminating unit 100*b*, the third line sensor 34*c* of the first imaging unit 30*a* scans the board 2 through the third lens 32*c*. The fourth line sensor 34*d* of the fourth imaging unit 30*d* scans through the fourth lens 32*d*. When a line has been scanned, the movement control unit 163 of the master PC 160 feeds a control signal to the board transport motor 58. The board transport motor 58 moves the board 2 by one line by moving the board transport table 50.

The scanned image obtained by the first imaging unit 30*a* is transmitted to the first image processing unit 130*a*, the image obtained by the second imaging unit 30*b* is transmitted to the second image processing unit 130*b*, the image obtained by the third imaging unit 30*c* is transmitted to the third image processing unit 130*c* and the image obtained by the fourth imaging unit 130*d* is transmitted to the fourth image processing unit 130*d*. Each of the image processing units 130 processes the received image. The first image processing unit 130*a* transmits the processed image to a memory 141*a* of the first slave PC 140*a* and stores the image therein. The second image processing unit 130*b* transmits the processed image to a memory 141*b* of the second slave PC 140*b* and stores the image therein. The third image processing unit 130*c* transmits the processed image to a memory 141*c* of the third slave PC 140*c* and stores the image therein. The fourth image processing unit 130*d* transmits the processed image to a memory 141*d* of the fourth slave PC 140*d* and stores the image stores the image therein.

The analyzing unit 142 (a generic reference to each of analyzing units in the slave PCs 140) in each of the slave PCs 140 refers to the image stored in an associated memory 141 (a generic reference to the memory provided in each of the slave PC 140*s*) so as to analyze data for sharing necessary for inspection of the board 2 in the other slave PCs 140. The data for sharing include positional data in an identification mark indicating the position of the board 2, identification data such as the serial number and the fabrication date of the board 2 obtained by analyzing the identification mark such as a bar code provided on the board 2, images of components captured both by the first imaging unit 30*a* and the second imaging unit 30*b*, as well as other data necessary for inspection of the board 2.

When the analyzing unit 142 has acquired data for sharing necessary for inspection of the board 2 by analyzing the image, the analyzing unit 142 stores the data or sharing in the memory 141 and transmits the data for sharing to the other slave PCs 140.

The analyzing unit 142 of the slave PC 140 receiving the data for sharing refers to the received data for sharing so as to analyze the image stored in the memory 141 and inspects the board 2 in accordance with determination criteria stored in a determination criteria storage unit 143. Thus, the slave PCs can share the data in a system wherein the multiple imaging units 30 capture images of the board 2 and the slave PCs 140 provided for the respective imaging units inspect the board 2. Therefore, precision in inspection of the board is improved and inspection time is reduced.

The images of the board 2, the data for sharing including positional data in an identification mark and the like, and the results of inspection of the board 2 by the slave PCs 140 are stored in the memories of the slave PCs and transmitted to the master PC 160. The master PC allows screen display of error locations of the board 2 as necessary, in accordance with the images of the board 2 and the results of inspection of the board 2.

It is to be understood that the invention is not limited by the embodiment as described above. It is also within the scope of the present invention to combine elements of the embodiment as appropriate. Modifications within the scope of the present invention such as design modifications can also be made to the embodiment on the basis of the knowledge of the skilled person. Some examples of such modifications will be described below.

Instead of scanning the board 2, the imaging units 30 may capture images of selected ranges successively by using a CCD sensor or the like. According to this modification, images of the board 2 can be captured easily.

Only one imaging unit 30 and one associated slave PC 140 may be provided above the board 2 for inspection of one surface thereof, and one each may be provided below the board 2 for inspection of the other surface. According to this approach, the number of slave PCs 140 can be reduced and the cost is curtailed accordingly.

The board 2 may be fixed and the illuminating units 100 and the imaging units 30 may be moved instead. According to this modification, relative movement between the imaging units 30 and the board 2 is achieved while the board 2 is held in a stable manner for imaging.

Second Embodiment

A description will be given of a background art related to a second embodiment of the present invention. Recently, electronic boards are used in a vast majority of equipment. Miniaturization, slim size and the like are persistent goals to be achieved in equipment in which electronic boards are used. For this purposes, high-integration design of an electronic board is required. For the purpose of achieving high-density mounting on an electronic board, it is important to inspect the condition in which components are mounted on a board with high precision. In the related art, there is proposed an inspection apparatus in which image recognition technology is used to inspect a printed board (hereinafter, referred to as a "board") on which components are already mounted with high precision (see, for example, patent document No. 3). There is also known an appearance inspection system in which multiple appearance inspection apparatuses and a personal computer (PC) for management are connected to each other via a LAN, in which a specified one of the appearance inspection apparatuses stores, as a final inspection result, results of inspection by the other appearance inspection apparatuses as well as a result of inspection by the specified appearance inspection apparatus, and in which the final inspection result is displayed on a monitor screen of the PC as a sole final result on a given board (see, for example, patent document No. 4). There is also known an appearance inspection apparatus capable of performing inspection of components mounted on both surfaces of a board simultaneously without mutual interference (see, for example, patent document No. 5).

(Patent Document No. 3)

Publication of examined application No. 7-120421

(Patent Document No. 4)

JP 11-118439 A (Patent Document No. 5)

JP 2003-99758

Meanwhile, the variety of inspection pieces is expanding year by year to extent that inspection pieces of the same kind sometimes differ in dimension such as thickness and height in an imaging direction. Accordingly, the structure of an appearance inspection apparatus needs to accommodate variation in the dimension of an inspection piece in an imaging direction, in order to conduct inspection with precision.

Accordingly, a primary purpose of the second embodiment is to provide an appearance inspection apparatus capable of inspecting with high precision even if the dimension of an inspection piece in an imaging direction varies from piece to piece.

A description will now be given of means to solve the problem addressed by the second embodiment. The appearance inspection apparatus according to the embodiment comprises: an imaging unit which is capable of capturing an image of the inspection piece and which is provided with a focusing mechanism for focusing on the inspection piece in accordance with the dimension of the inspection piece in an imaging direction, without changing an image magnification factor.

The imaging unit of the appearance inspection apparatus is provided with a focusing mechanism for focusing on the inspection piece in accordance with the dimension of the inspection piece in an imaging direction, without changing an image amplification factor. Thus, according to this appearance inspection apparatus, a clear, well-focused image of an inspection piece is obtained even when the dimension of an inspection piece in an imaging direction varies from piece to piece. Accordingly, high-precision inspection is enabled.

In this case, the focusing mechanism preferably varies the focal distance from the inspection piece in accordance with the thickness of the inspection piece. Such a structure is suitable for inspection of an inspection piece such as a board having substantially uniform thickness.

The imaging unit preferably includes a front imaging unit for capturing an image of the front surface of the inspection piece and a back imaging unit for capturing an image of the back surface of the inspection piece, and at least one of the front imaging unit and the back imaging unit is provided with the focusing mechanism.

That is, since an inspection piece containing objects of inspection on both surfaces is positioned such that the position of one of the front surface and the back surface is determined with respect to a corresponding imaging unit, the focusing mechanism may be provided in at least one of the front imaging unit and the back imaging unit.

According to the second embodiment, it is possible to conduct inspection with high precision even if the dimension of an inspection piece in an imaging direction varies from piece to piece.

A detailed description of the best mode of carrying out the embodiment will be given below with reference to the drawings.

Figure 6:
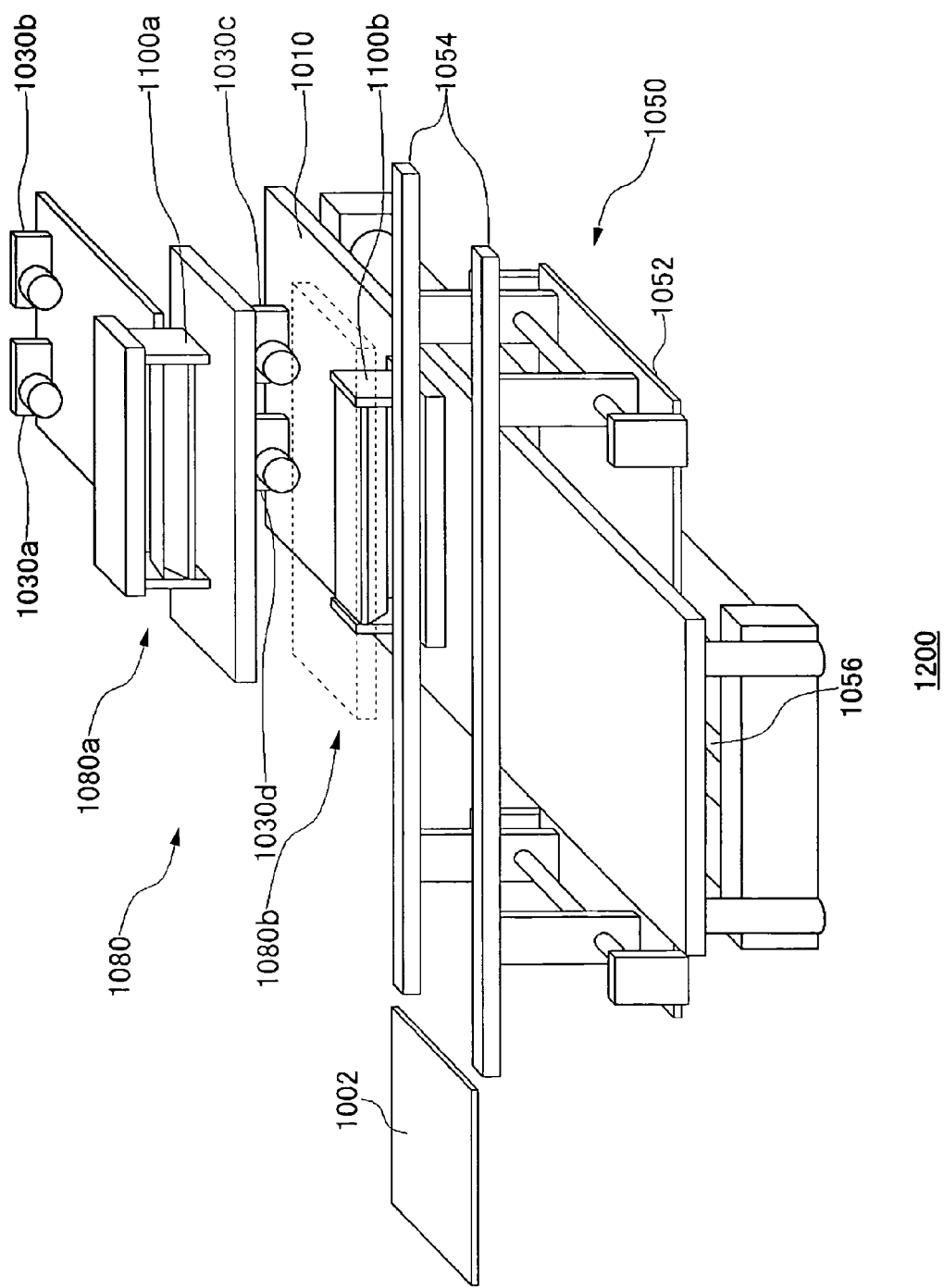
FIG. 6 shows the structure of an appearance inspection apparatus according to a second embodiment of the present invention.

FIG. 6 is an enlarged perspective view of an appearance inspection apparatus according to the second embodiment. An appearance inspection apparatus 1200 shown in FIG. 6 includes an inspection table 1010, a board transport table 1050, a front imaging unit 1080*a* and a back imaging unit 1080*b* (generically, referred to as imaging units 1080). The board transport table 1050 is provided with a support plate 1052 and two transport rails 1054 supported by the support plate 1052. A transport belt (not shown) driven by a motor (not shown) to transport a board 1002 (inspection piece) is provided to each of the transport rails 1054. The board 1002 is transported nearly to the center of the inspection table 1010 by the transport belts. A transport sensor (not shown) using a noncontact sensor such as an optical sensor (not shown) for detecting the board 1002 transported is provided above the transport rails 1054. When the transport sensor detects the end face of the board 1002 or a detection hole provided in the board 1002, it is determined that the board 1002 is transported nearly to the center of the inspection table 1010, whereupon the transportation of the board 1002 by the transport belts is halted. The board 1002 of the second embodiment is an electronic board in which electronic components such as IC chips and connectors are mounted. The front surface of the board 1002 is a reflow surface and the back surface is a DIP surface.

The board transport table 1050 is provided with an insertion unit into which is inserted a guide shaft provided in the lower part of the appearance inspection apparatus 1200. The board transport table 1050 is supported by the guide shaft so as to be movable in a direction perpendicular to the direction in which the transport rails 1054 transport the board 1002. Further, the board transport table 1050 is engaged with a feed screw 1056 driven by a transport motor 1058 (see FIG. 9). By rotating the feed screw (ball screw) 1056, the board transport table 1050 is moved to transport the board 1002 as far as the imaging units 1080.

The front transport rail 54 illustrated in FIG. 6 is provided with a clamp (not shown) for correcting the configuration of the board 1002 by pressing downward the board 1002 mounted on the transport rails 1054.

Figure 7:
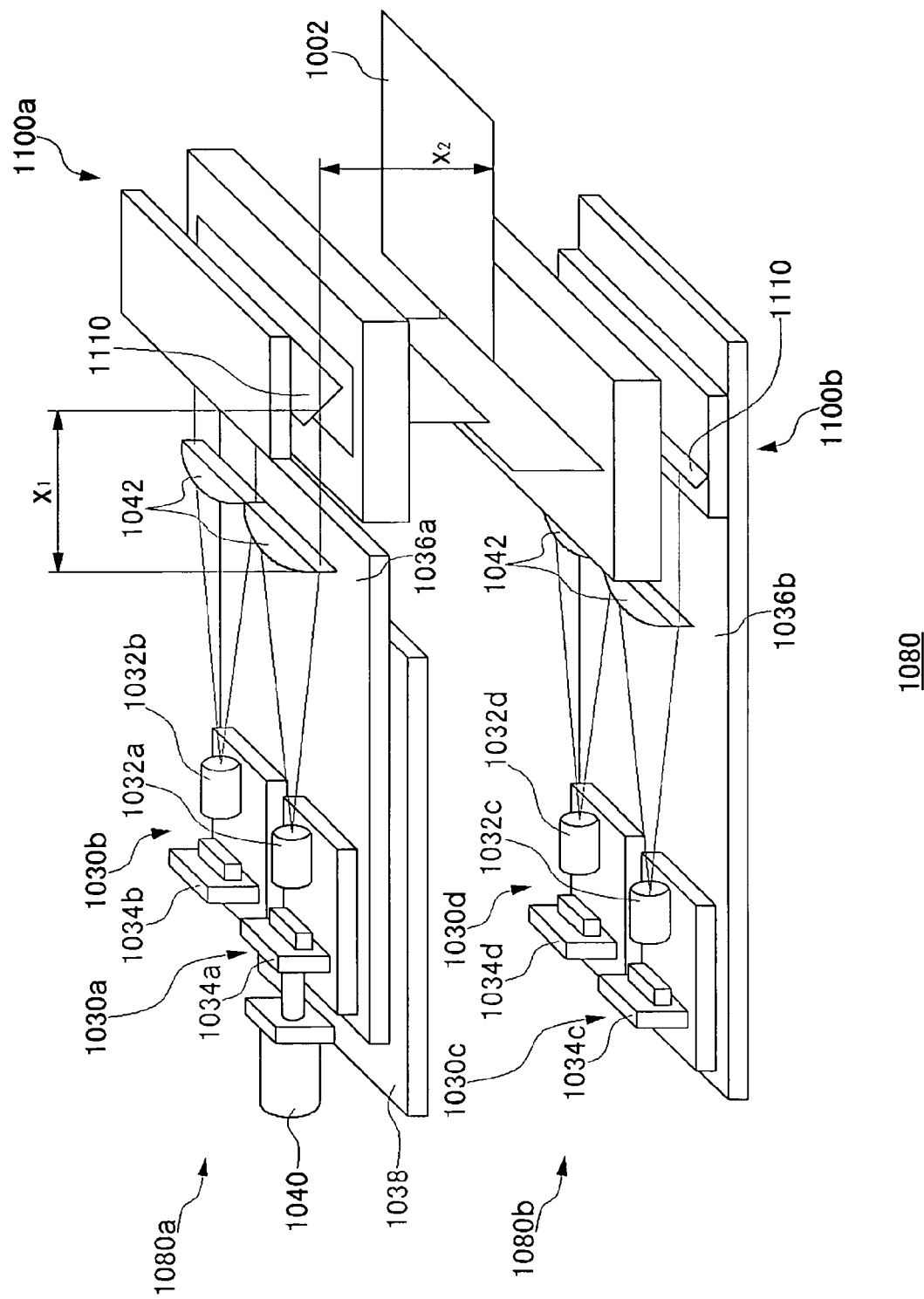
FIG. 7 shows the structure of an imaging system according to the second embodiment.

FIG. 7 is an enlarged perspective view showing imaging units 1080 included in the appearance inspection apparatus 1200. As shown in FIG. 7, the imaging units 1080 include a front imaging unit 1080a for capturing an image of the front surface (reflow surface) of the board 1002 from above and a back imaging unit 1080b for capturing an image of the back surface (DIP surface) of the board 1002 from below. As shown in FIG. 7, the front imaging system 1080a is provided above the transport rails 1054. The back imaging system 1080b is provided below the transport rails 1054 so as to sandwich the board 1002 (inspection piece) with the front imaging system 1080a.

The front imaging unit 1080a comprises a front illuminating unit 100a, a front support frame 1036a, a base frame 1038, a first imaging unit 1030a, a second imaging unit 1030b, a focusing motor 1040, an intermediate lens 1042 and the like. The back imaging unit 1080b comprises a back illuminating unit 1100b, a back support frame 1036b, a third imaging unit 1030c, a fourth imaging unit 1030d, an intermediate lens 1042 and the like. Hereinafter, the first imaging unit 1030a, the second imaging unit 1030b, the third imaging unit 1030c and the fourth imaging unit 1030d will generically be referred to as imaging units 1030, and the front illuminating unit 1100a and the back illuminating unit 1100b will generically be referred to as illuminating units 1100.

As shown in FIG. 7, the first imaging unit 1030a, the second imaging unit 1030b and the intermediate lens 1042 are permanently mounted on the front support frame 1036a. The first imaging unit 1030a comprises a first lens 1032a and a first line sensor 1034a. The second imaging unit 1030b comprises a second lens 1032b and a second line sensor 1034b. The first imaging unit 1030a and the second imaging unit 1030b are provided side by side above the board 1002 in order to capture an image of the front surface of the board 1002. Arrangement of the first lens 1032a, the first line sensor 1034a, the second lens 1032b, the second line sensor 1034b and the intermediate lens 1042 is determined such that the imaging ranges of the first imaging unit 1030a and the second imaging unit 1030b overlap. By using multiple imaging units 1030a and 1030b, an image of the front surface of the board 1002 can be captured with high resolution so that inspection precision is improved. Since a captured image is subject to distributed image processing by using multiple imaging units 1030a and 1030b, inspection speed is also improved.

The front support frame 1036a of the front imaging unit 1080a is supported by the base frame 1038 so as to be slidable in a direction in which the board 1002 is transported. The front support frame 1036a is driven by the focusing motor 1040 to slide with respect to the base frame 1038. By driving the focusing motor 1040, the first imaging unit 1030a, the second imaging unit 1030b and the intermediate lens 1042 fixed to the front support frame 1036a are moved as a unit with respect to the base frame 1038.

The third imaging unit 1030c, the fourth imaging unit 1030d and the intermediate lens 1042 of the back imaging unit 1080b are fixed to the back support frame 1036b located below the base frame 1038 and the like. The third imaging unit 1030c and the fourth imaging unit 1030d of the back imaging unit 1080b are provided side by side below the board 1002 in order to capture an image of the back surface of the board 1002. Arrangement of the third lens 1032c, the third line sensor 1034c, the fourth lens 1032d, the fourth line sensor 1034d and the intermediate lens 1042 is also determined such that the imaging ranges of the third imaging unit 1030c and the fourth imaging unit 1030d overlap.

Figure 8:
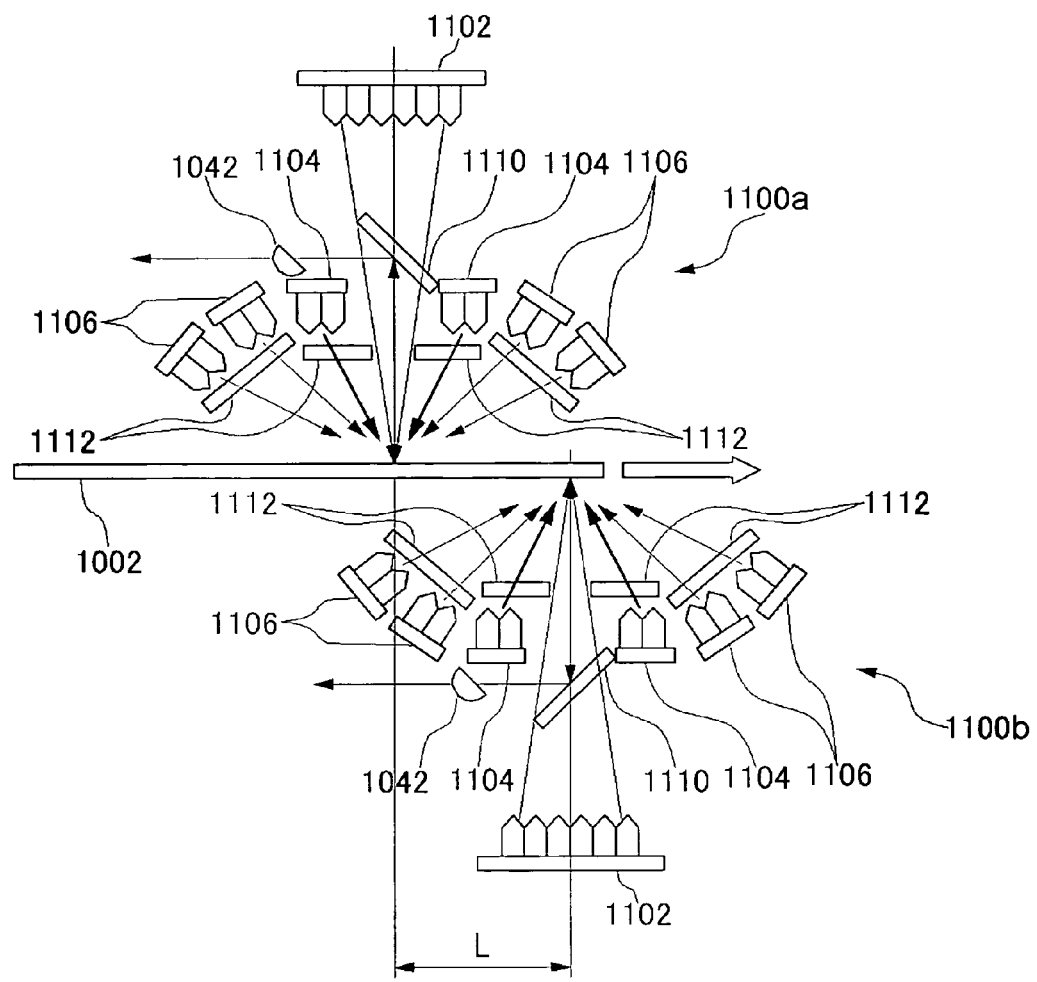
FIG. 8 shows the structure of an illuminating unit according to the second embodiment.

FIG. 8 is a schematic view showing the structure of the illuminating units 1100 included in the imaging units 1080. The illuminating units 1100 include the front illuminating unit 1100a of the front imaging unit 1080a and the back illuminating unit 1100b of the back imaging unit 1080b. Each of the front illuminating unit 1100a and the back illuminating unit 1100b comprises a first light source 1102, a second light source 1104, a third light source 1106, a half mirror 1110, an acrylic sheet 1112 and the like. The first light source 1102, the second light source 1104 and the third light source 1106 are arranged to surround the half mirror 1110.

The first light source 1102 comprises a group of green light emitting diodes (LEDs) arranged in the scanning direction of the first and second line sensors 1034a and 1034b or the scanning direction of the third and fourth line sensors 1034c and 1034d. The green diodes extend in a length equal to or longer than the width of the board 1002. The first light source 1102 of the front illuminating unit 1100a is provided immediately above a scanned line on the board 1002 scanned by the line sensors 1034a and 1034b of the front imaging unit 1080a for substantially perpendicular incident illumination of the board 2 below. In contrast, the first light source 1102 of the back illuminating unit 1100b is provided immediately below a scanned line on the board 1002 scanned by the line sensors 1034c and 1034d of the back imaging unit 1080b for substantially perpendicular incident illumination of the board 1002 above.

The angle of incidence of light emitted by the first light source 1102 and incident on the inspected surface of the board 1002 via the half mirror 1110 is substantially zero. In this embodiment, the first light source 1102 is designed to provide a certain beam width, ensuring that some light components are incident on the board 1002 at an angle of incidence of zero, even if the board 1002 is warped. Light reflected from the board 1002 (scanned line) is reflected by the half mirror 1100 and is transmitted through the intermediate lens 1042 before being incident on a set of the first lens 1032a and the second lens 1032b, or on a set of the third lens 1032c and the fourth lens 1032d. By using the first light source 1102 for incident illumination of the board 1002 and detecting the light by the line sensors 1034, displacement of components, missing components and solder wetting characteristics on the board 1002 can be determined. For efficient incident illumination of a scanned line, the board populated with the LED group may be divided in the middle into two sub-boards each of which carries a group of LEDs.

The second light source 1104 comprises a group of white light emitting diodes (LEDs) arranged in the scanning direction of the first and second line sensors 1034a and 1034b or the scanning direction of the third and fourth line sensors 1034c and 1034d. The white diodes extend in a length equal to or longer than the width of the board 1002. Each of the illuminating units 1100a and 1100b is provided with two second light sources 1104 which are provided to sandwich a scanned line on the board 1002 in the direction in which the board 1002 is transported so as not to interfere with incident illumination of the scanned line by the first light source 1102.

The third light source 1106 comprises a group of blue LEDs arranged in the scanning direction of the first and second line sensors 1034a and 1034b or the scanning direction of the third and fourth line sensors 1034c and 1034d. The blue diodes extend in a length equal to or longer than the width of the board 1002. Each of the illuminating units 1100a and 1100b is provided with four third light sources 1106 (two on each side) sandwiching a scanned line on the board 1002 in the direction in which the board 1002 is transported so as not to interfere with illumination of the scanned line by the first light source 1102 and the second light source 1104.

As described above, the first light source 1102 emits green light, the second light source 1104 emits white light and the third light source 1106 emits blue light. Thus, each of the illuminating units 1100a and 1100b functions as a composite light source illuminating the board 1002 with multiple colors. A green LED and a blue LED are brighter than a white LED. Accordingly, by designing the first light source 1102 to emit green light and the third light source 1106 to emit blue light, a clear image with a high S/N ratio is obtained. Since a majority of printed boards are green in color, the first light source designed as a source of green light achieves bright incident illumination on the plane. Characters and the like printed by laser on components such as an IC chip or a connector mounted on the board 1002 are properly recognizable by designing the third light source 11106 as a source of blue light and by illuminating the components with blue light at a low angle.

In this embodiment, the acrylic sheet 1112 for diffusing light from the second light source 1104 and the third light source 1106 is provided between the second light source 1104 and a scanned line and between the third light source 1106 and the scanned line. Thus, even when each of the second light source 1104 and the third light source 1106 comprises a set of LEDs as point light sources, the diffusive action minimizes the occurrence of a spot light presenting itself as a reflected image and impairing inspection precision. In this embodiment, the second light source 1104 emitting while light, the first light source 1102 emitting green light and the third light source 1106 emitting blue light are driven independently in the stated order so as to illuminate a scanned line three times. In each illumination, the line sensors 1034 scan the board 1002. In this way, images of the board 1002 as illuminated by the light sources 1102, 1104 and 1106 are obtained.

There may be a hole provided in the board 1002 or a hole may remain incompletely filled with solder. In such a instance, light from one of the illuminating units 1100 may leak to the other of the illuminating units 1100 via the hole. In case light leaked to the other of the illuminating units 1100 is directly scanned by the line sensors 34, a phenomenon called blooming occurs, which may adversely affect imaging of the board 1002. Therefore, the front illuminating unit 1100a and the back illuminating unit 1100b in this embodiment are provided with an offset of L with respect to each other in the direction in which the board is transported. That is, as seen in FIG. 8, the front illuminating unit 1100a is provided upstream of the back illuminating unit 1100b in the direction in which the board is transported. The offset L may preferably be 50 mm or longer in respect of suppression of blooming.

Figure 9:
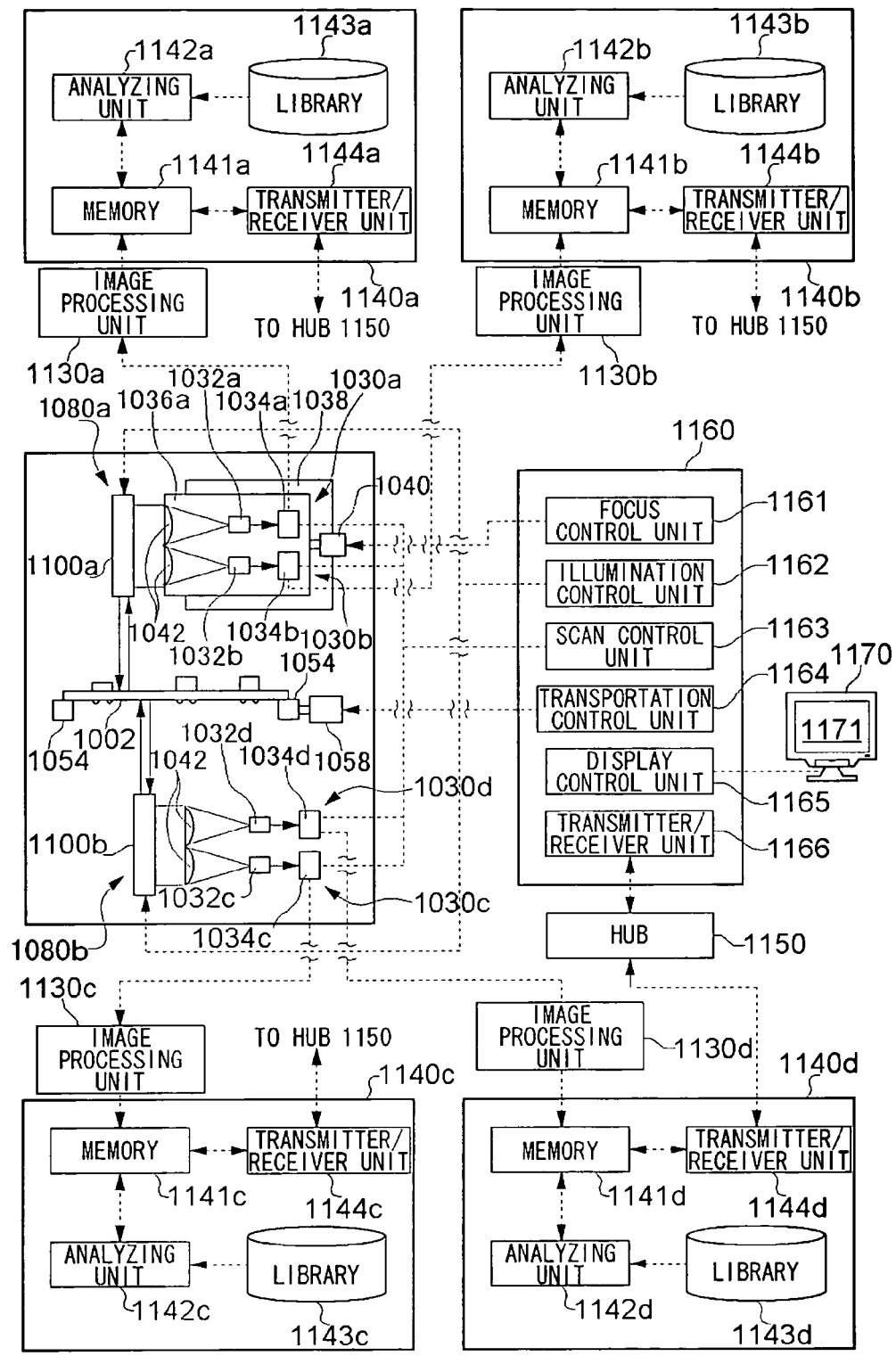
FIG. 9 shows the structure of an appearance inspection apparatus according to the second embodiment in which slave personal computers as inspecting units are included.

FIG. 9 is a control block diagram of the appearance inspection apparatus 1200. As shown in FIG. 9, the first line sensor 1034a included in the first imaging unit 1030a of the front imaging unit 1080a is connected to a first slave PC 1140a (inspecting unit) via a first image processing unit 1130a. The second line sensor 1034b included in the second imaging unit 1030b of the front imaging unit 1080a is connected to a second slave PC 1140b via a second image processing unit 1130b. The first slave PC 1140a and the second slave PC 1140b function as front surface inspecting units corresponding to the front imaging unit 1080a.

Similarly, the third line sensor 1034c included in the third imaging unit 1030c of the back imaging unit 1080b is connected to a third slave PC 1140c (inspecting unit) via a third image processing unit 1130c. The fourth line sensor 1034d included in the fourth imaging unit 1030d of the back imaging unit 1080b is connected to a fourth slave PC 1140d via a fourth image processing unit 1130d. The third slave PC 1140c and the fourth slave PC 1140d function as back surface inspecting units corresponding to the back imaging unit 1080b. Hereinafter, the first image processing unit 1130a, the second image processing unit 1130b, the third image processing unit 1130c and the fourth image processing unit 1130d will generically be referred to as image processing units 1130. The first slave PC 1140a, the second slave PC 1140b, the third slave PC 1140c and the fourth slave PC 1140d will generically be referred to as slave PCs 1140. Each of the image processing units 1130 processes an image captured by a corresponding imaging unit 1030 so as to generate image data.

In addition to a CPU, ROM and RAM, the slave PCs 1140a-1140d are respectively provided with memories 1141a-1141d for storing image data and the like transmitted from the image processing units 1130a-1130d, respectively. Analyzing units 1142a-1142d that use the CPU and the like to analyze and inspect the image data stored in the memories 1141a-1141d, respectively, are built in the slave PCs 1140a-1140d, respectively. Further, the slave PCs 1140a-1140d are provided with libraries 1143a-1143d storing inspection data used for analysis by the analyzing units 1142a-1142d as determination criteria for determining whether the board 1002 passes the inspection. The slave PCs 1140a-1140d are also provided with transmitter and receiver units 1144a-1144d for data transmission and reception.

Each of the transmitter and receiver units 1144a-1144d of the slave PCs 1140a-1140d is connected to the other slave PCs via a switching hub 1150 to enable mutual data communication. The slave PCs 1140a-1140d are also connected to a master PC 1160 via the switching hub 1150. In this way, data communication between the master PC 1160 and each of the slave PCs 1140a-1140d is also enabled. The master PC 1160 is provided with a CPU, a ROM, a RAM, a memory and an input/output interface. The master PC 1160 functions as a managing unit for managing the appearance inspection apparatus 1200 as a whole. A focus control unit 1161, an illumination control unit 1162, a scan control unit 1163 and a transport control unit 1164 are built in the master PC 1160 by using a CPU and the like. The master PC 1160 is also provided with a display control unit 1165 and a transmitter and receiver unit 1166 for data transmission and reception. As shown in FIG. 9, the display control unit 1165 controls a display 1170 for displaying a final inspection result, and the transmitter and receiver unit 1166 is connected to the switching hub 1150.

The focus control unit 1161 controls the focusing motor 1040 provided in the front imaging unit 1080a. In this embodiment, the focus control unit 1161, the focusing motor 1040, and the sliding mechanism provided between the front support frame 1036a and the base frame 1038 constitute a focusing mechanism for focusing on the board 1002 without changing an image magnification factor. The illumination control unit 1162 controls the front illuminating unit 1100a and the back illuminating unit 1100b. The scan control unit 1163 controls the scanning of the inspected piece by the first line sensor 1034a and the second line sensor 1034b of the front imaging unit 1080a and by the third line sensor 1034c and the fourth line sensor 1034d of the back imaging unit 1080b. Further, the transport control unit 1164 controls the transport motor 1058. Transportation of the board 1002 set up on the transport rails 1054 (transport belts) and line-by-line movement of the board 1002 are controlled by the transport control unit 1164.

The transmitter and receiver unit 1166 of the master PC 1160 may be connected to the other PCs and the like via a local area network (LAN). In this way, the master PC 1160 is allowed to supply an inspection result to the other PCs and the like. An input/output unit such as a keyboard and a mouse (not shown) is connected to the master PC 1160. A user is capable of performing an operation such as data input to the appearance inspection apparatus 1200 via the keyboard and the like.

A procedure for appearance inspection of an inspection piece by the appearance inspection apparatus 11200 will now be described with reference to FIGS. 10-14.

Figure 10:
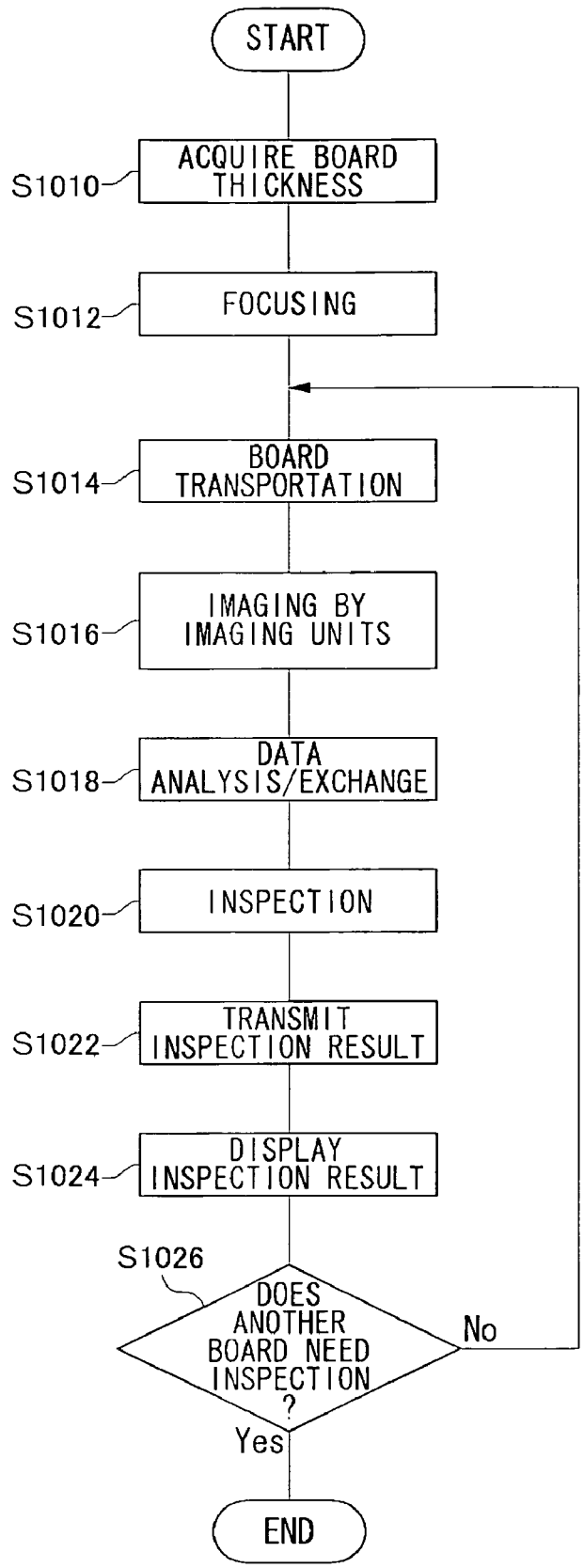
FIG. 10 is a schematic view showing the structure of an appearance inspection apparatus according to the second embodiment.

FIG. 10 is a flow chart showing a procedure for appearance inspection of the board 1002 by the appearance inspection apparatus 1200. FIG. 10 shows a procedure for simultaneously inspecting the front surface and the back surface of the board 1002 on which components such as IC chips and connectors are mounted through a reflow process on the front surface of the board and a DIP process on the back surface of the board. As shown in FIG. 10, inspection of the board 1002 is started by the focus control unit 1161 of the master PC 1160 referring to board information (inspection data) input before the inspection so as to acquire information on the thickness of the board 1002 from (S1010). The thickness of the board 1002 may be input to the master PC 1160 by a user by using a keyboard or a mouse. Once the thickness of the board 1002 is acquired, the focus control unit 1161 of the master PC 1160 reads, from a focus control adjustment table stored in a predetermined storage area, the amount of movement (for example, on the order of 0.3-2.0 mm) of the front support frame 1036a with respect to the base frame 1038 proportional to the thickness of the board 1002 input in S1010. The focus control unit 1161 controls the focusing motor 1040 so as to move the front support frame 1036a by the amount thus read (S1012).

As already described, the first and second line sensors 1034a and 1034b, the first and second lenses 1032a and 1032b, the intermediate lens 1042 and the like constituting an imaging system (optical system) of the front imaging unit 1080a are fixed on the front support frame 1036a. Therefore, as a result of the front support frame 1036a being moved with respect to the base frame 1038, the focal distance between the board (inspection piece) and the lens (i.e. a total of a distance x1001 between the end face of the intermediate lens 1042 and the half mirror 1100 and a distance x1002 between the half mirror 1110 and the surface of the board 1002) (see FIG. 12) changes. As a result, focusing on the board 1002 is achieved without changing an image amplification factor. Thus, the appearance inspection apparatus 1200 is provided with a focusing mechanism for varying the focal distance (x1001+ x1002) from the board 1002 in accordance with the dimension of the board 1002 in an imaging direction (i.e. in accordance with the thickness of the board 1002). As a result, the appearance inspection apparatus 1200 achieves focusing on the surface of the board 1002 and allows a clear image to be obtained, even if the thickness of the board 1002 varies from board to board. Accordingly, inspection can be performed with high precision.

When the focusing process in S1012 is completed, the transport control unit 1164 of the master PC 1160 causes the board transport table 1050 to start transporting the board 1002 as far as the imaging units 1080 (S1014). As already described, the front illuminating unit 1100a is provided upstream of the back illuminating unit 1100b in the direction in which the board 1002 is transported. Therefore, the board 1002 is initially moved by the board transport table 1050 to a start position within the scanning range of the first line sensor 1034a and the second line sensor 1034b of the front imaging unit 1080a. When the board 1002 is transported as far as a start position within the scanning range of the first line sensor 1034a and the second line sensor 1034b of the front imaging unit 1080a, the illumination control unit 1162 of the master PC 1160 causes the front illuminating unit 1100a and the back illuminating unit 1100b to start illuminating the board 1002. The scan control unit 1163 of the master PC 1160 causes the first and second imaging units 1030a and 1030b of the front imaging unit 1080a and the third and fourth imaging units 1030c and 1030d of the back imaging unit 1080b to start capturing images of the front and back surfaces of the board 1002 (S1016).

When imaging by the imaging units 1080a and 1080b is started in S1016, the first line sensor 1034a, the second line sensor 1034b, the third line sensor 1034c and the fourth line sensor 1034d are controlled by the scan control unit 1163 to synchronously scan the board 1002 in each unit scanning step. When the front surface of the board 1002 is illuminated by the front illuminating unit 1100a with light, the first line sensor 1034a of the first imaging unit 1030a scans the board 1002 through the intermediate lens 1042 and the first lens 1032a. The second line sensor 1034b of the second imaging unit 1030b scans through the intermediate lens 1042 and the second lens 1032b. When the back surface of the board 1002 is illuminated by the back illuminating unit 1100b with light, the third line sensor 1034c of the third imaging unit 1030c scans the board 1002 through the intermediate lens 1042 and the third lens 1032c. The fourth line sensor 1034d of the fourth imaging unit 1030d scans through the intermediate lens 1042 and the fourth lens 1032d. In this way, by using the line sensors 1034a-1034d, the mechanism is simplified and inspection time is reduced as compared with a related-art structure in which an inspected surface is made to travel in two dimensions and then halted, which steps are repeated for successive spot images to be taken.

Each time the board 1002 is scanned one line by the first through fourth line sensors 1034a-1034d, the transport control unit 1164 of the master PC 1160 supplies a control signal to the transport motor 1058 for driving the feed screw 1056 so as to advance the board 1002 by one line. In this way, scanning by the first through fourth line sensors 1034a-1034d can be performed in one sitting. The board 1002 can be moved by the transport control unit 1164 while scanning by the first through fourth line sensors 1034a-1034d is not being performed. Therefore, the board 1002 is scanned efficiently so that inspection time is reduced. A unit scanning step is a unit step of scanning operation each of the line sensors 1034a-1034d is capable of performing. For example, a unit scanning step refers to a one-way scan from one end of the board 1002 to the other or a two-way scan.

By allowing the first through fourth line sensors 1034a-1034d to scan the entire length of the board 1002 in the direction in which the board 1002 is transported, imaging of both surfaces of the board 1002 is completed in a single board transportation process. That is, the board 1002 is transported by the board transport table 1050 between the front imaging unit 1080a and the back imaging unit 1080b. The front imaging unit 1080a captures an image of the front surface of the board 1002 in a single transportation process, and the back imaging unit 1080b captures an image of the back surface of the board 1002 in a single transportation process. The term "single transportation process" may refer to a process whereby the board 1002 is transported in one direction only or a process whereby the board 1002 reciprocates.

In this embodiment, the illumination control unit 1162 controls the front illuminating unit 1100a and the back illuminating unit 1100b so that illumination associated with the execution of each unit scanning step is performed synchronously while images of the board 1002 are being captured by the imaging units 1080a and 1080b. The scan control unit 1163 controls the first through fourth line sensors 1034a-1034d so that scanning of the board 1002 is performed synchronously while the front illuminating unit 1100a and the back illuminating unit 1100b are illuminating the board 1002 with light.

More specifically, the illumination control unit 1162 controls the front illuminating unit 1100a and the back illuminating unit 1100b to simultaneously illuminate the board 1002 with light of the same color. In this embodiment, the second light source 1104 emitting while light, the first light source 1102 emitting green light and the third light source 1106 emitting blue light are driven in the stated order so that the front illuminating unit 1100a and the back illuminating unit 1100b illuminate the board 1002 with white light, green light and blue light in the stated order. Therefore, even if light from the front illuminating unit 1100a leaks to the back surface of the board 1002 illuminated by the back illuminating unit 1100b, as a result of a peripheral component presenting itself as a reflected image, adverse effects of optical interference on the inspection result are minimized.

When the second light sources 1104 of the front illuminating unit 1100a and the back illuminating unit 1100b simultaneously illuminate the board 1002 with white light, the scan control unit 1163 of the master PC 1160 causes the line sensors 1034a-1034d to perform a unit scanning step synchronously. When the first light sources 1102 of the front illuminating unit 1100a and the back illuminating unit 1100b simultaneously illuminate the board 1002 with green light, the scan control unit 1163 causes the line sensors 1034a-1034d to perform an additional unit scanning step synchronously. When the third light sources 1106 of the front illuminating unit 1100a and the back illuminating unit 1100b simultaneously illuminate the board 1002 with blue light, the scan control unit 1163 causes the line sensors 1034a-1034d to perform a still additional unit scanning step synchronously.

As the imaging units 1080a and 1080b capture images of the board 1002, the image obtained by the first line sensor 1034a of the first imaging unit 1030a is transmitted to the first image processing unit 1130a, the image obtained by the second line sensor 1034b of the second imaging unit 1030b is transmitted to the second image processing unit 1130b, the image obtained by the third line sensor 1034c of the third imaging unit 1030c is transmitted to the third image processing unit 1130c, and the image obtained by the fourth line sensor 1034d of the fourth imaging unit 1030d is transmitted to the fourth image processing unit 1130d.

Each of the image processing units 1130a-1130d processes the image from a corresponding one of the line sensors 1034a-1034d. The first image processing unit 1130a transmits the processed image to the memory 1141a of the first slave PC 1140a and stores the image therein. The second image processing unit 1130b transmits the processed image to the memory 1141b of the second slave PC 1140b and stores the image therein. Similarly, the third image processing unit 1130c transmits the processed image to the memory 1141c of the third slave PC 1140c and stores the image therein. The fourth image processing unit 1130d transmits the processed image to the memory 1141d of the fourth slave PC 1140d and stores the image therein.

When imaging of the board 1002 by the front imaging unit 1080a and the back imaging unit 1080b is completed, the transport control unit 1164 of the master PC 1160 moves the board transport table 1050 by supplying an instruction signal to the transport motor 1058 and rotating the feed screw 1056 accordingly, so as to carry the board 1002 for which imaging is completed to a subsequent fabrication step.

When the image data of the board 1002 is stored in each of the memories 1141a-1141d of the slave PCs 1140a-1140d, each of the analyzing units 1142a-1142d of the respective slave PCs 1140a-1140d analyzes the image data stored in a corresponding one of the memories 1141a-1141d. Data necessary for inspection of the board 1002 are exchanged between the slave PCs 1140a-1140d (S1018). Data exchanged in S1018 between the slave PCs 1140a-1140d include data to be shared by the slave PCs 1140a-1140d in inspecting the board 1002 (hereinafter, referred to as data for sharing) and images of components captured by the first imaging unit 1030a, the second imaging unit 1030b, the third imaging unit 1030c and the fourth imaging unit 1030d. Data for sharing include data indicating the position of an identification mark on the board 1002 that serves as a reference for positioning, and data such as the serial number and the fabrication date of the board 1002 obtained by analyzing a tag mark such as a bar code provided on the board 1002.

Figure 11A:
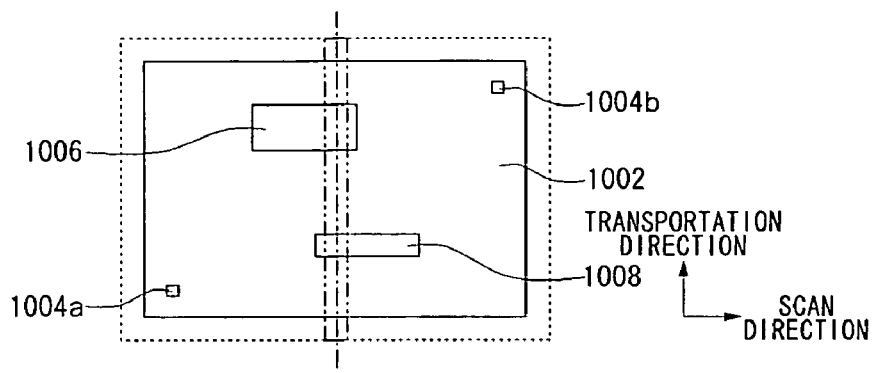
FIG. 11A is a top view showing the surface of a substrate (inspection piece)

A description will now be given of image data analysis/exchange in S1018, with reference to FIGS. 11A-11C. FIG. 11A is a top view showing the surface of the board 1002. The following description concerns analysis of image data of the surface of the board 1002 and sharing of data. As shown in FIG. 11A, the board 1002 is provided with a first identification mark 1004a and a second identification mark 1004b that serve as references for positioning of the board 1002. Further, a first component 1006 and a second component 1008 are provided substantially at the center of the board 1002 shown in FIG. 11A to extend across the imaging ranges of the first and second imaging units 1030a and 1030b of front imaging unit 1080a. A bar code (not shown) storing various data is provided on the board 1002.

As shown in FIG. 11A, an image of the left-half area in the board 1002 as illustrated is captured by the first imaging unit 1030a and an image of the right-half area is captured by the second imaging unit 1030b. Accordingly, an image of the first identification mark 1004a of the board 1002 is captured by the first imaging unit 1030a and associated image data is stored in the memory 1141a of the first slave PC 1140a. An image of the second identification mark 1004b of the board 1002 is captured by the second imaging unit 1030b and associated image data is stored the memory 1141b of the second slave PC 1140b. This allows the slave PC 1140a corresponding to the first imaging unit 1030a to acquire position data from the image data of the identification mark, when analyzing the image data stored in the memory 1141a. Similarly, the slave PC 1140b corresponding to the second imaging unit 1030b acquires position data from the image data of the identification mark, when analyzing the image data stored in the memory 1141b. The first slave PC 1140a transmits the position data derived from the first identification mark 1004a to the other slave PCs 1140b, 1140c and 1140d as data for sharing. The second slave PC 1140*b* transmits the position data derived from the second identification mark 1004*b* to the other slave PCs 1140*a*, 1140*c* and 1140*d*.

As a result, it is possible to address a situation in which the board 1002 is slightly inclined on the transport rails 1054, or the board 1002 is slightly displaced with respect to an ideal position in the scan direction or the transportation direction. More specifically, by allowing the position data, derived from the first identification mark 1004*a* and the second identification mark 1004*b* as references for positioning of the board 1002, to be shared by the slave PCs 1140*a*-1140*d*, the slave PCs 1140*a*-1140*d* can have the knowledge of the position and orientation of the board 1002 even if the an identification mark is not included in the imaging range of the corresponding imaging units 1030*a*-1030*d* or if only some of the identification marks are included in the range.

As shown in FIG. 11A, an overlapping imaging range denoted by an alternate long and two short dashes line is provided between the imaging range of the first imaging unit 1030*a* and the imaging range of the second imaging unit 1030*b* so as not to create a range not scanned by either of the first imaging unit 1030*a* and the second imaging unit 1030*b* of the front imaging unit 1080*a*. Similarly, in the back imaging unit 1080*b*, an overlapping imaging range is provided between the imaging range of the third imaging unit 1030*c* and the imaging range of the fourth imaging unit 1030*d*. Taking an example of the front imaging unit 1080*a*, the imaging range of the first imaging unit 1030*a* extends from the left end of the board 1002 as illustrated in FIG. 11B and slightly into the right half thereof beyond the center line lying in the direction of scan of the board 1002. The imaging range of the second imaging unit 1030*b* extends from the right end of the board 1002 as illustrated and slightly into the left half thereof beyond the center line lying in the direction of scan of the board 1002.

Figure 11B:
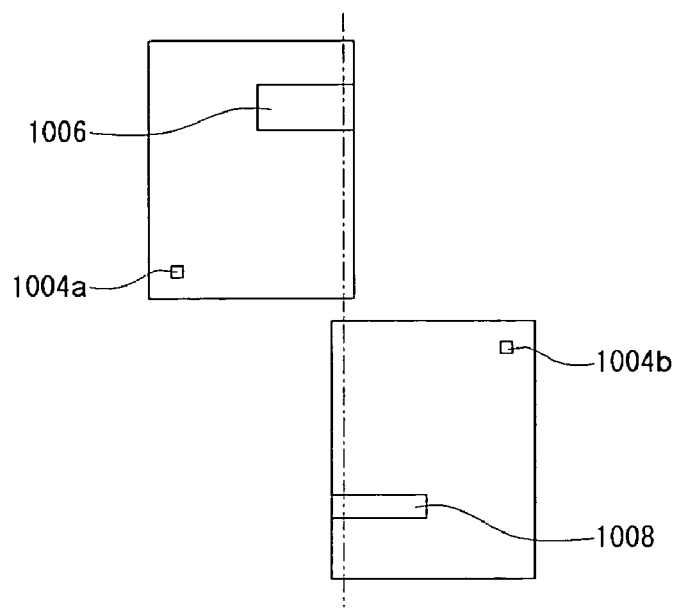
FIG. 11B is a schematic view showing imaging ranges of imaging units.
Figure 11C:
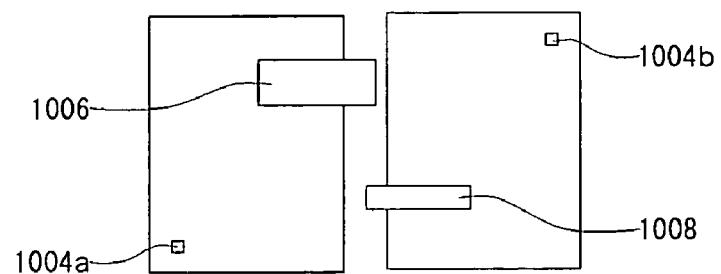
FIG. 11C is a schematic view for explaining about images stored in memories of slave personal computers as inspecting units.

As for components (for example, the first component 1006 and the second component 1008 illustrated in FIGS. 11A-11C) provided on the board 1002 to extend across the imaging ranges of multiple imaging units 1030, the task of inspecting such a component is assigned to a selected one of the slave PCs 1140 corresponding to one of the imaging units 1030 with an imaging range covering the center of the component. For example, as shown in FIG. 11A, the center of the first component 1006 is located within the imaging range of the first imaging unit 1030*a*. Therefore, the first slave PC 1140*a* (inspecting unit associated with the first imaging unit 1030*a*) is responsible for inspecting the first component 1006. Conversely, the second component 1008 is located with the imaging range of the second imaging unit 1030*b*. Therefore, the second slave PC 1140*b* (inspecting unit associated with the second imaging unit 1030*b*) is responsible for inspecting the second component 1008.

In this case, as shown in FIG. 11B, the slave PC 1140*a* does not hold the entirety of the image data of the first component 1006 to be inspected by the slave PC 1140*a*, at a point of time when the first image processing unit 1130*a* corresponding to the first imaging unit 1030*a* stores the image data in the memory 1141*a* of the slave PC 1140*a*. Similarly, the slave PC 1140*b* does not hold the entirety of the image data of the second component 1008 subject to its inspection, at a point of time when the second image processing unit 1130*b* corresponding to the second imaging unit 1030*b* stores the image data in the memory 1141*b* of the slave PC 1140*b*.

Thus, each of the slave PCs 1140*a*-1140*d*, upon recognizing image data of a component not subject to its inspection while analyzing image data, transmits the recognized image data to one of the slave PCs 1140*a*-1140*d* responsible for the inspection of that component (or to other slave PCs 1140*a*-1140*d*). That is, in the example of FIGS. 11A-11C, the memory 1141*a* of the first slave PC 1140*a* includes a portion of the image data of the second component 1008. The image data of the second component 1008 is transmitted from the first slave PC 1140*a* to the second slave PC 1140*b* responsible for the inspection of the second component 1008. The second slave PC 1140*b* stores the image data thus transmitted in the memory 1141*b*. Similarly, the memory 1141*b* of the second slave PC 1140*b* includes a portion of the image data of the first component 1006. The image data of the first component 1006 is transmitted from the second slave PC 1140*b* to the First slave PC 1140*a* responsible for the inspection of the first component 1006. The first slave PC 1140*a* stores the image data thus transmitted in the memory 1141*a*. Thus, as shown in FIG. 11C, each of the slave PCs 1140*a* and 1140*b* can acquire missing image data of a component subject to the PC's inspection.

When analysis/exchange of image data is completed, the analyzing units 1142*a*-1142*d* of the slave PCs 1140*a*-1140*d* perform inspection of respective areas on the board 1002 for which they are responsible, using inspection data stored in the libraries 1143*a*-1143*d* (S1020). In the appearance inspection apparatus 1200, there are provided multiple sets of inspection data which serve as references for determination as to whether a board passes the inspection, for individual components mounted on the board 1002 such as IC chips and connectors, as well as for respective imaging directions of the front imaging unit 1080*a* and the back imaging unit 1080*b*.

In the related-art appearance inspection apparatus, it is general that the front and back surface of the board are not simultaneously inspected. Therefore, the apparatus need not identify a soldering type such as reflow, DIP soldering or hand soldering in accordance with the direction of imaging by the imaging units. In contrast, the appearance inspection apparatus 1200 according to this embodiment is provided with at least one of front inspection data and back inspection data for each component mounted on the board 1002 so as to enable simultaneous inspection of both surfaces of the board 1002. The front inspection data and the back inspection data each comprises image data and numerical data specifying a solder configuration and the like that pass the inspection. Each inspection data includes an identifier for identifying a soldering type such as reflow, DIP soldering or hand soldering commensurate with the configuration of a solder pad corresponding to a component.

The front inspection data for each component is stored in the library 1142*a* or the library 1143*b* provided in the slave PC 1140*a* or the slave PC 1140*b* (both of which correspond to the front imaging unit 1080*a*), respectively, which is responsible for the inspection of the component. The back inspection data for each component is stored in the library 1143*c* or the library 1143*d* provided in the slave PC 1140*c* or the slave PC 1140*d* (both of which correspond to the back imaging unit 2080*b*), respectively, which is responsible for the inspection of the component. The front inspection data stored in the libraries 1142*a* and 1143*b* of the slave PCs 1140*a* and 1140*b* responsible for the inspection of the front surface of the board 1002 may be identical to each other. Similarly, the back inspection data stored in the libraries 1143*c* and 1143*d* of the slave PCs 1140*c* and 1140*d* responsible for the inspection of the back surface of the board 1002 may be identical to each other.

By using the front inspection data and back inspection data in combination with the image data of the board 1002 obtained by using the front imaging unit 1080*a* and the back imaging unit 1080*b* in the appearance inspection apparatus 1200, it is possible to scan the board 1002, which is provided with a reflow surface on the front and a DIP surface on the back, in multiple directions (i.e. from above and from below) with high precision. The front inspection data and back inspection data may be individually input to the libraries 1143a-1143d of the slave PCs 1140a-1140d. Alternatively, the entirety of front inspection data and back inspection data may be input to the master PC 1160 in one sitting so that the slave PCs 1140a-1140d acquire the necessary inspection data from the master PC 1160.

In this way, the slave PCs 1140a-1140d of the appearance inspection apparatus 1200 analyze the image data stored in the memories 1141a-1141d and share the resultant data that include an identification mark, bar code, and other data necessary for inspection. The slave PCs 1140a-1140d also exchange the image data necessary for inspection. The slave PCs 1140a-1140d perform the inspection of the board 1002 by using the data for sharing, the image data and the inspection data stored in the libraries 1143a-1143d.

The operation of the slave PCs 1140a-1140d described above is analogous to the workings of a cell inside a living organism. The cells have identical genes and select only those instructions related to them for execution, in accordance with a trigger. Analogy can be drawn between this and the second embodiment in that the data for sharing corresponds to genes and the slave PCs 1140a-1140d correspond to cells. In this embodiment, instead of the master PC 1160 assigning inspection locations and inspection menus to the slave PCs 1140a-1140d and directing the PCs accordingly, the slave PCs 1140 autonomously process image data and perform inspection. As a result, it is possible in the appearance inspection apparatus 1200 to improve precision with which the board 1002 is inspected and reduce inspection time, by allowing the multiple slave PCs 1140a-1140d to share the workload of inspecting the board 1002.

When the inspection in S1020 is completed, each of the slave PCs 1140a-1140d transmits data indicating a result of inspection to the other slave PCs 1140 and the master PC 1160 so as to share the result of inspection with each other (S1022). The data for sharing such as position data stored in the memories 1141a-1141d of the slave PCs 1140a-1140d and derived from identification marks are also transmitted to the master PC 1160. In accordance with an instruction from the CPU, the display controller 1165 of the master PC 1160 causes the result of inspection of the board 1002 on a screen 1171 of a display 1171, by referring to preset CAD data of the board 1002 and the data received from the slave PCs 1140a-1140d (S1024).

Figure 12:
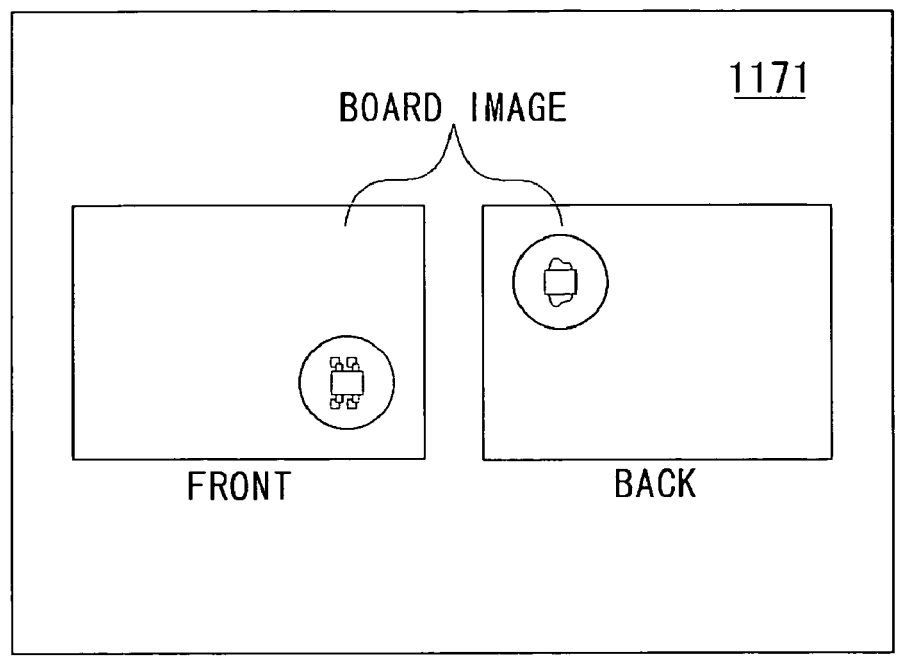
FIG. 12 is a schematic view showing results of inspection displayed on a display included in the appearance inspection apparatus of FIG. 6.

FIG. 12 is a schematic view showing an inspection result displayed on the screen 1171 of the display 1170. As shown in FIG. 12, the display control unit 1165 of the appearance inspection apparatus 1200 according to this embodiment causes the result of inspection of the front surface of the board 1002 and the result of the inspection of the back surface of the board 1002 to be displayed on the screen 1171 of the display 1170 simultaneously. As shown in FIG. 12, the display control unit 1165 also causes the inspection result to be displayed on the screen 1171 such that locations (components) identified by the slave PCs 1140a-1140d to contain a failure are displayed in a manner clearly distinguishable from locations that pass the inspection. In this way, a user can gain the knowledge of the inspection result of both the front surface of an inspection piece and the back surface thereof without mouse operation or the like. Thus, it will be appreciated that the appearance inspection apparatus 1200 presents to a user the inspection result of both the front surface of the board 1002 and the back surface thereof simultaneously, after both surfaces of the board 1002 have been efficiently inspected. Accordingly, usability for users is significantly improved.

Figure 13:
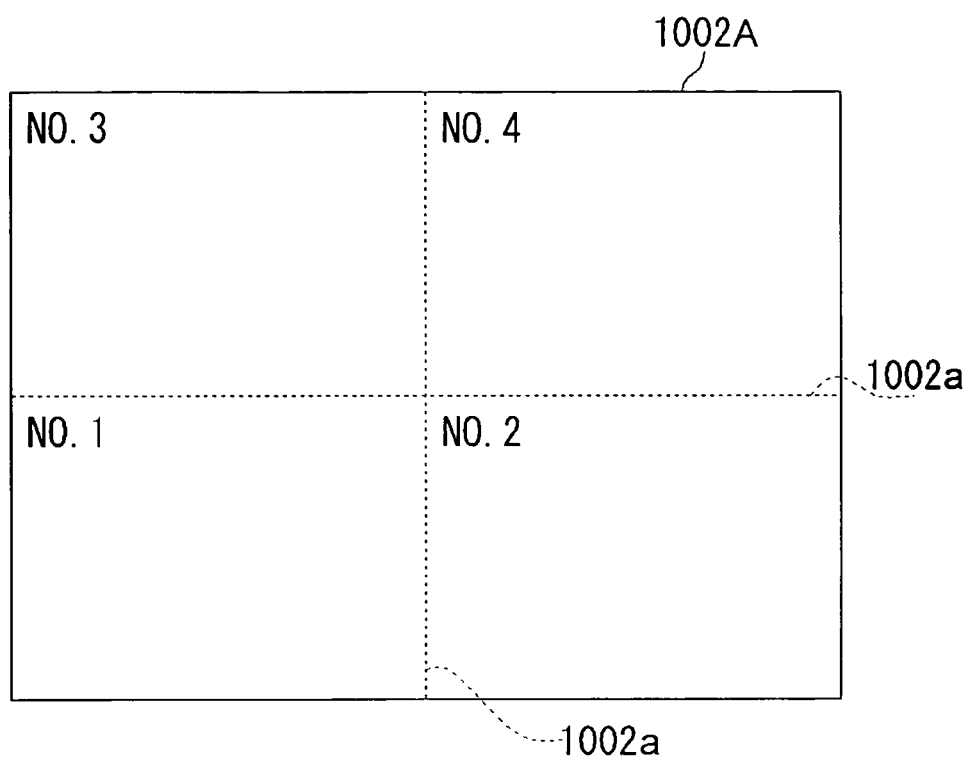
FIG. 13 is a schematic view showing an inspection piece subject to inspection by the appearance inspection apparatus of FIG. 6.
Figure 14:
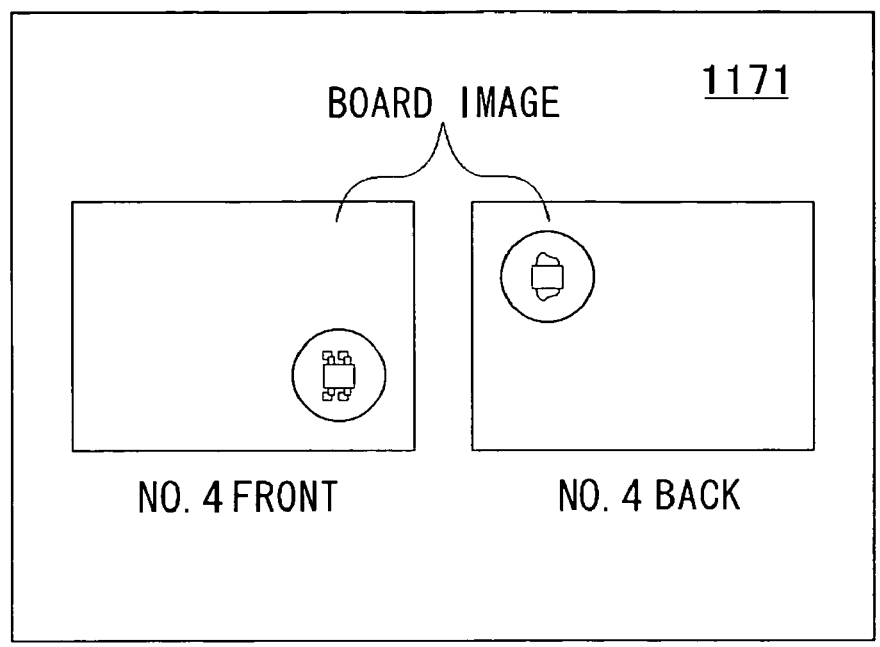
FIG. 14 is a schematic view showing results of inspection displayed on the display included in the appearance inspection apparatus of FIG. 6.

In case the inspection piece is a board 1002A of a type provided with perforations, V notches 1002a or the like as illustrated in FIG. 13 so as to be severed after components have been mounted, the result of inspection by the slave PCs 1140a-1140d may be displayed on the screen 1171 of the display 1170 in a manner illustrated in FIG. 14. That is, if, as a result of inspection by the slave PCs 1140a-1140d of the board 1002A severed as shown in FIG. 13 into four areas No. 1001-No. 1004 after components have been mounted, defects are found in both surfaces of area No. 1004, the display control unit 1165 of the master PC 1160 only causes the front and back surfaces of area No. 1004 containing defects to be displayed on the screen 1171 of the display 1170. By allowing only the front and back surfaces of a selected area in the board 1002A determined to contain a defect as a result of inspection by the slave PCs 1140a-1140d to be displayed on the display 1170, usability for users is significantly improved.

When the result of inspection by the slave PCs 1140a-1140d has been displayed on the display 1170, the master PC 1160 determines whether a similar inspection piece needs inspection (S1026). If it is determined that there is a similar inspection piece, i.e. if it is determined that the board 1002 having the same thickness as the board 1002 for which inspection is completed needs inspection (Yes in S1026), the master PC 1160 causes steps in S1014-S1024 to be performed again. If it is determined that there is not a similar inspection piece (No in S1026), the master PC 1160 terminates inspection by the appearance inspection apparatus 1200.

It is to be understood that the embodiment is not limited by the preferred example as described above. It is also within the scope of the embodiment to make various modifications and changes on the basis of the knowledge of those skilled in the art. Some examples of such modifications will be described below.

Instead of scanning the board 1002 by the line sensors 1034a-1034d, the imaging units 1030a-1030d may capture images of selected ranges successively by using a CCD sensor or the like. According to this modification, images of the board 1002 can be captured equally easily.

Only one imaging unit 1030 and one associated slave PC 1140 may be provided to face the front surface of the board 1002, i.e. above the board 1002, and one each may be provided to face the back surface of the board 1002, i.e. below the board 1002. According to this modification, the number of imaging units 1030 and slave PCs 1140 is reduced so that the cost is curtailed accordingly. In this case, the data for sharing is exchanged between the slave PC 1140 for inspecting the front surface of the board 1002 and the slave PC 1140 for inspecting the back surface. Consequently, provision of an identification mark on one of the surfaces of the board 1002 may be omitted. Inspection is still enabled by using positional data derived from an identification mark on the other surface. As a result, the structure of the board 1002 is simplified.

The imaging unit 1080 including the illuminating units 1100 and the imaging units 1030 may be moved, while the board 1002 is fixed. According to this modification, relative movement of the imaging unit 1080 and the board 1002 is achieved while the board 1002 is maintained in a stable state for imaging of the board 1002.

The data for sharing may be transmitted from the master PC 1160 to the slave PCs 1140 after the slave PCs 1140 transmitted the same to the master PC 1160. In this way, the slave PCs 1140 and the master PC 1160 can share the data easily.

In the embodiment described above, only the front imaging unit 1080a is provided with a focusing mechanism. Alternatively, both the front imaging unit 1080a and the back imaging unit 1080b may be provided with a focusing mechanism depending on the configuration of an inspection piece.

Although a procedure for inspecting both surfaces of the board 1002 simultaneously is described above, the result of inspection of the front surface of the inspection piece and the result of inspection of the back surface of the inspection piece may be acquired through different steps and displayed simultaneously. One of the result of inspection of the front surface and the result of inspection of the back surface may be acquired in another appearance inspection apparatus.

In the embodiment described above, it is assumed that a user inputs the thickness of the board necessary for focusing. Alternatively, the bar code on the board may contain information on the thickness of the board so that focusing is performed when an image of the bar code has been captured and analyzed.

Needless to say, the appearance inspection apparatus according to this embodiment can be used for pre-reflow inspection.

Third Embodiment

A description will first be given of the background for a third embodiment of the present invention. Recently, electronic boards are used in a vast majority of equipment. Miniaturization, slim size, low price and the like are persistent goals to be achieved in equipment in which electronic boards are used. For this purposes, high-integration design of an electronic board is required. For the purpose of achieving high-density mounting on an electronic board, it is important to inspect the condition in which components are mounted on a board with high precision. In the related art, there is proposed an inspection apparatus in which image recognition technology is used to inspect a printed board (hereinafter, referred to as a "board") on which components are already mounted with high precision. There is also known an appearance inspection system in which multiple appearance inspection apparatuses and a personal computer (PC) for management are connected to each other via a LAN, in which a specified one of the appearance inspection apparatuses stores, as a final inspection result, results of inspection by the other appearance inspection apparatuses as well as a result of inspection by the specified appearance inspection apparatus, and in which the final inspection result is displayed on a monitor screen of the PC as a sole final result on a given board (see, for example, patent document No. 3). There is also known an appearance inspection apparatus capable of performing inspection of components mounted on both surfaces of a board simultaneously without mutual interference (see, for example, patent document No. 4).

[Patent Document No. 3]

Publication of examined application No. 7-120421

[Patent Document No. 4]

JP 11-118439 A

[Patent Document No. 5]

JP 2003-99758 A

A description will now be given of a problem to be solved by the third embodiment. In the related-art appearance inspection apparatuses as described above, the inspection result is generally displayed on a display screen. In the process of displaying the result, mouse operation or the like may be necessary in order for a user to view a necessary result. That is, from the perspective of improvement in usability for users, the related-art appearance inspection apparatuses have room for improvement in respect of a manner in which the inspection result is displayed. Particularly, display of results of inspection of both surfaces of an inspection piece needs modification so that users can understand the result properly.

Accordingly, a primary purpose of the third embodiment is to provide an appearance inspection apparatus in which a result of inspection of an inspection piece is displayed in an easily understandable manner and in which usability for users is improved.

A description will now be given of means to solve the problem addressed by this embodiment. The appearance inspection apparatus according to this embodiment comprises: a display unit which displays a result of inspection of the inspection piece; and a result display control unit which causes a result of inspection of the front surface of the inspection piece and a result of inspection of the back surface of the inspection piece to be displayed on the display unit simultaneously.

When employed for an inspection piece in which objects to be inspected are located on both surfaces thereof, the appearance inspection apparatus according to this embodiment allows a result of inspection of the front surface of the inspection piece and a result of inspection of the back surface thereof to be displayed simultaneously. In this way, a user can gain the knowledge of the results of inspection of both surfaces of the inspection piece simultaneously without any extra operation. Therefore, usability for users is improved. The result of inspection of the front surface of the inspection piece and the result of inspection of the back surface of the inspection piece may be acquired through different steps or acquired substantially simultaneously. One of the result of inspection of the front surface and the result of inspection of the back surface may be acquired in another appearance inspection apparatus.

The appearance inspection apparatus may further comprise: a front imaging unit which captures an image of the front surface of the inspection piece; a front inspecting unit which is provided to correspond to the front imaging unit and which inspects the inspection piece by referring to image data of the inspection piece obtained by using the front imaging unit; a back imaging unit which captures an image of the back surface of the inspection piece; and a back inspecting unit which is provided to correspond to the back imaging unit and which inspects the inspection piece by referring to image data of the inspection piece obtained by using the back imaging unit, wherein the result display control unit receives a result of inspection from each of the front inspecting unit and the back inspecting unit and causes the result of inspection of the front surface and the result of inspection of the back surface to be displayed on the display unit simultaneously.

By employing such a structure, it is possible to inspect both surfaces of an inspection piece efficiently using a single appearance inspection apparatus. Additionally, by presenting the results of inspection of both surfaces of the inspection piece to a user simultaneously, usability for users is improved.

Preferably, the front imaging unit and the back imaging unit capture images of the inspection piece substantially simultaneously.

In this way, both surfaces of an inspection piece can be inspected simultaneously and inspection efficiency is improved.

According to this embodiment, a result of inspection of an inspection piece by an appearance inspection apparatus can be displayed in an easily understandable manner and usability for users is improved.

A detailed description will now be given of an example of practicing the embodiment with reference to the drawings.

Figure 15:
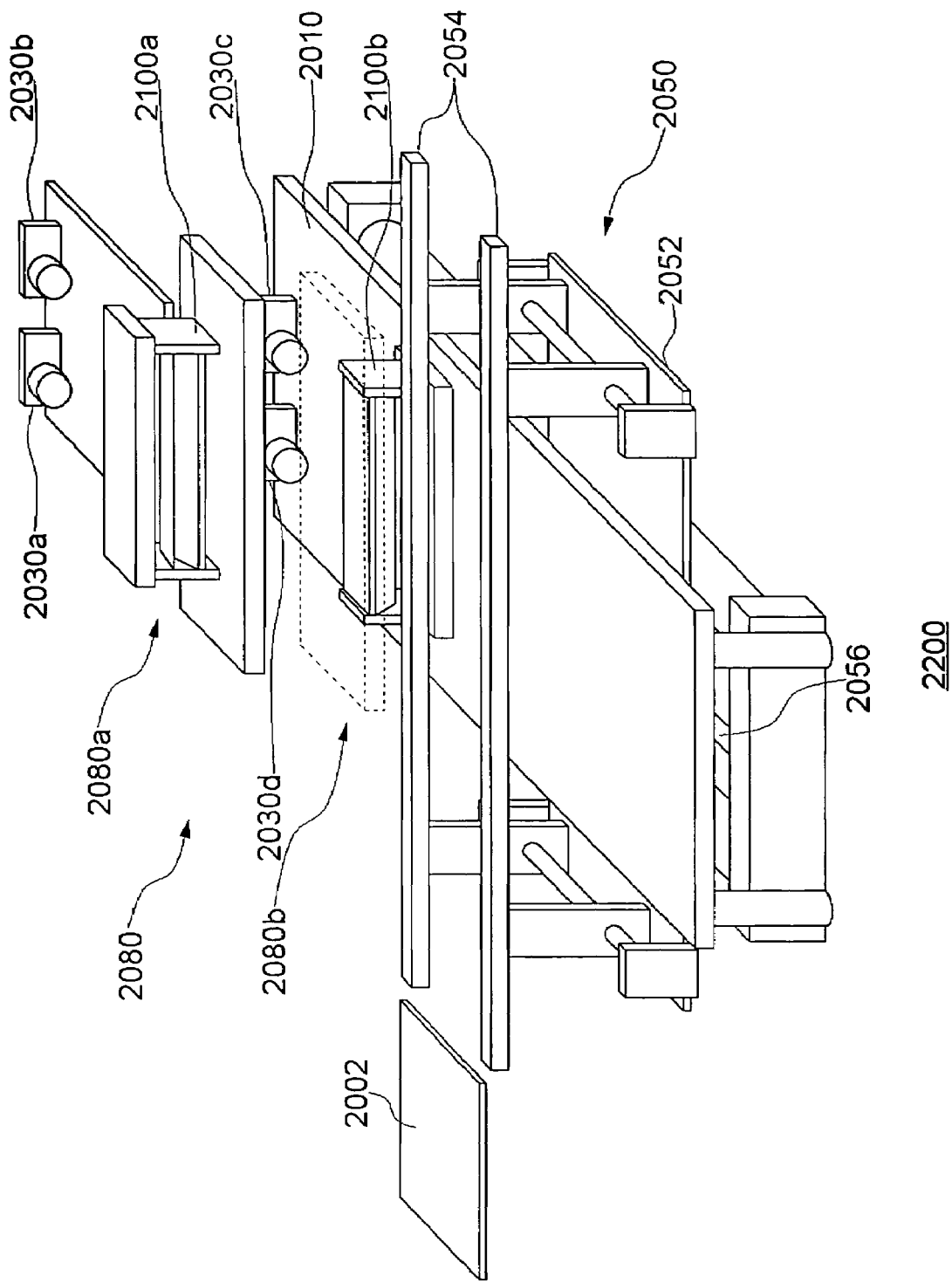
FIG. 15 is an enlarged perspective view of the appearance inspection apparatus according to a third embodiment of the present invention.

FIG. 15 is an enlarged perspective view of an appearance inspection apparatus according to the third embodiment. An appearance inspection apparatus 2200 shown in FIG. 15 includes an inspection table 2010, a board transport table 2050, a front imaging unit 2080a and a back imaging unit 2080b (generically, referred to as imaging units 2080). The board transport table 2050 is provided with a support plate 2052 and two transport rails 2054 supported by the support plate 2052. A transport belt (not shown) driven by a motor (not shown) to transport a board 2002 (inspection piece) is provided to each of the transport rails 2054. The board 2002 is transported nearly to the center of the inspection table 2010 by the transport belts. A transport sensor (not shown) using a noncontact sensor such as an optical sensor for detecting the board 2002 transported is provided above the transport rails 2054 and practically at the center of the inspection table. When the transport sensor detects the end face of the board 2002 or a detection hole provided in the board 2002, it is determined that the board 2002 is transported nearly to the center of the inspection table 1010, whereupon the transportation of the board 2002 by the transport belts is halted. The board 2002 of the third embodiment is an electronic board in which electronic components such as IC chips and connectors are mounted. The front surface of the board 2002 is a reflow surface and the back surface is a DIP surface.

The board transport table 2050 is provided with an insertion unit into which is inserted a guide shaft provided in the lower part of the appearance inspection apparatus 2200. The board transport table 2050 is supported by the guide shaft so as to be movable in a direction perpendicular to the direction in which the transport rails 2054 transport the board 2002. Further, the board transport table 2050 is engaged with a feed screw 2056 driven by a transport motor 2058 (see FIG. 18). By rotating the feed screw (ball screw) 2056, the board transport table 2050 is moved to transport the board 2002 as far as the imaging units 2080. The front transport rail 2054 illustrated in FIG. 15 is provided with a clamp (not shown) for correcting the configuration of the board 2002 by pressing downward the board 2002 mounted on the transport rails 2054.

Figure 16:
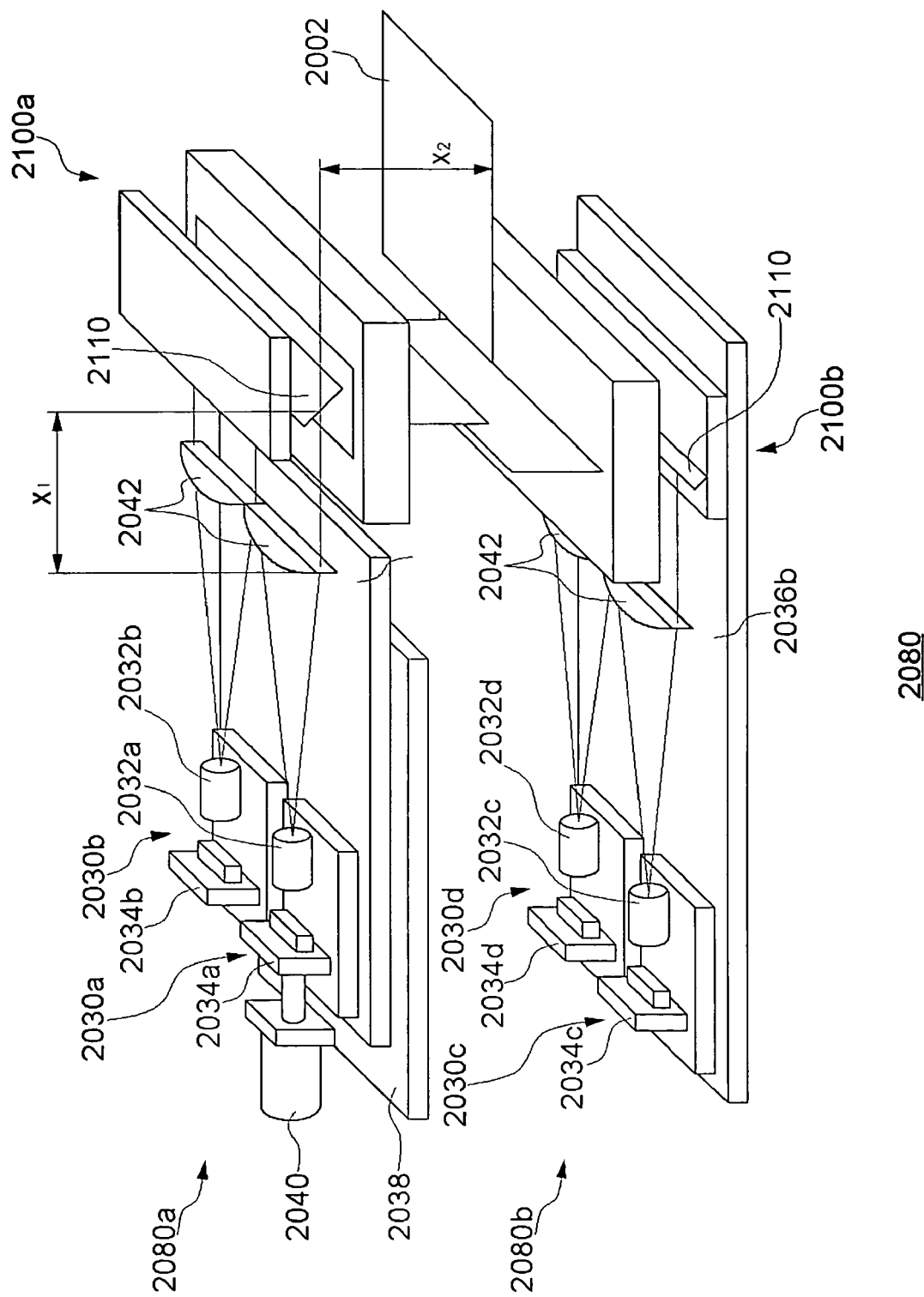
FIG. 16 is an enlarged perspective view showing an imaging unit included in the appearance inspection apparatus of FIG. 15.

FIG. 16 is an enlarged perspective view showing imaging units 2080 included in the appearance inspection apparatus 2200. As shown in FIG. 16, the imaging units 2080 include a front imaging unit 2080a for capturing an image of the front surface (reflow surface) of the board 2002 from above and a back imaging unit 2080b for capturing an image of the back surface (DIP surface) of the board 2002 from below. As shown in FIG. 16, the front imaging system 2080a is provided above the transport rails 2054. The back imaging system 2080b is provided below the transport rails 2054 so as to sandwich the board 2002 (inspection piece) with the front imaging system 2080a.

The front imaging unit 2080a comprises a front illuminating unit 2100a, a front support frame 2036a, a base frame 2038, a first imaging unit 2030a, a second imaging unit 2030b, a focusing motor 2040, an intermediate lens 2042 and the like. The back imaging unit 2080b comprises a back illuminating unit 2100b, a back support frame 2036b, a third imaging unit 2030c, a fourth imaging unit 2030d, an intermediate lens 2042 and the like. Hereinafter, the first imaging unit 2030a, the second imaging unit 2030b, the third imaging unit 2030c and the fourth imaging unit 2030d will generically be referred to as imaging units 2030, and the front illuminating unit 2100a and the back illuminating unit 2100b will generically be referred to as illuminating units 2100.

As shown in FIG. 16, the first imaging unit 2030a, the second imaging unit 2030b and the intermediate lens 2042 are permanently mounted on the front support frame 2036a. The first imaging unit 2030a comprises a first lens 2032a and a first line sensor 2034a. The second imaging unit 2030b comprises a second lens 2032b and a second line sensor 2034b. The first imaging unit 2030a and the second imaging unit 2030b are provided side by side above the board 2002 in order to capture an image of the front surface of the board 2002. Arrangement of the first lens 2032a, the first line sensor 2034a, the second lens 2032b, the second line sensor 2034b and the intermediate lens 2042 is determined such that the imaging ranges of the first imaging unit 2030a and the second imaging unit 2030b overlap. By using multiple imaging units 2030a and 030b, an image of the front surface of the board 1002 can be captured with high resolution so that inspection precision is improved. Since a captured image is subject to distributed image processing by using multiple imaging units 2030a and 2030b, inspection speed is also improved.

The front support frame 2036a of the front imaging unit 2080a is supported by the base frame 2038 so as to be slidable in a direction in which the board 2002 is transported. The front support frame 2036a is driven by the focusing motor 2040 to slide with respect to the base frame 2038. By driving the focusing motor 2040, the first imaging unit 2030a, the second imaging unit 2030b and the intermediate lens 2042 fixed to the front support frame 2036a are moved as a unit with respect to the base frame 2038.

The third imaging unit 2030c, the fourth imaging unit 2030d and the intermediate lens 2042 of the back imaging unit 2080b are fixed to the back support frame 2036b located below the base frame 2038 and the like. The third imaging unit 2030c and the fourth imaging unit 2030d of the back imaging unit 2080b are provided side by side below the board 2002 in order to capture an image of the back surface of the board 2002. Arrangement of the third lens 2032c, the third line sensor 2034c, the fourth lens 2032d, the fourth line sensor 2034d and the intermediate lens 2042 is also determined such that the imaging ranges of the third imaging unit 2030c and the fourth imaging unit 2030d overlap.

Figure 17:
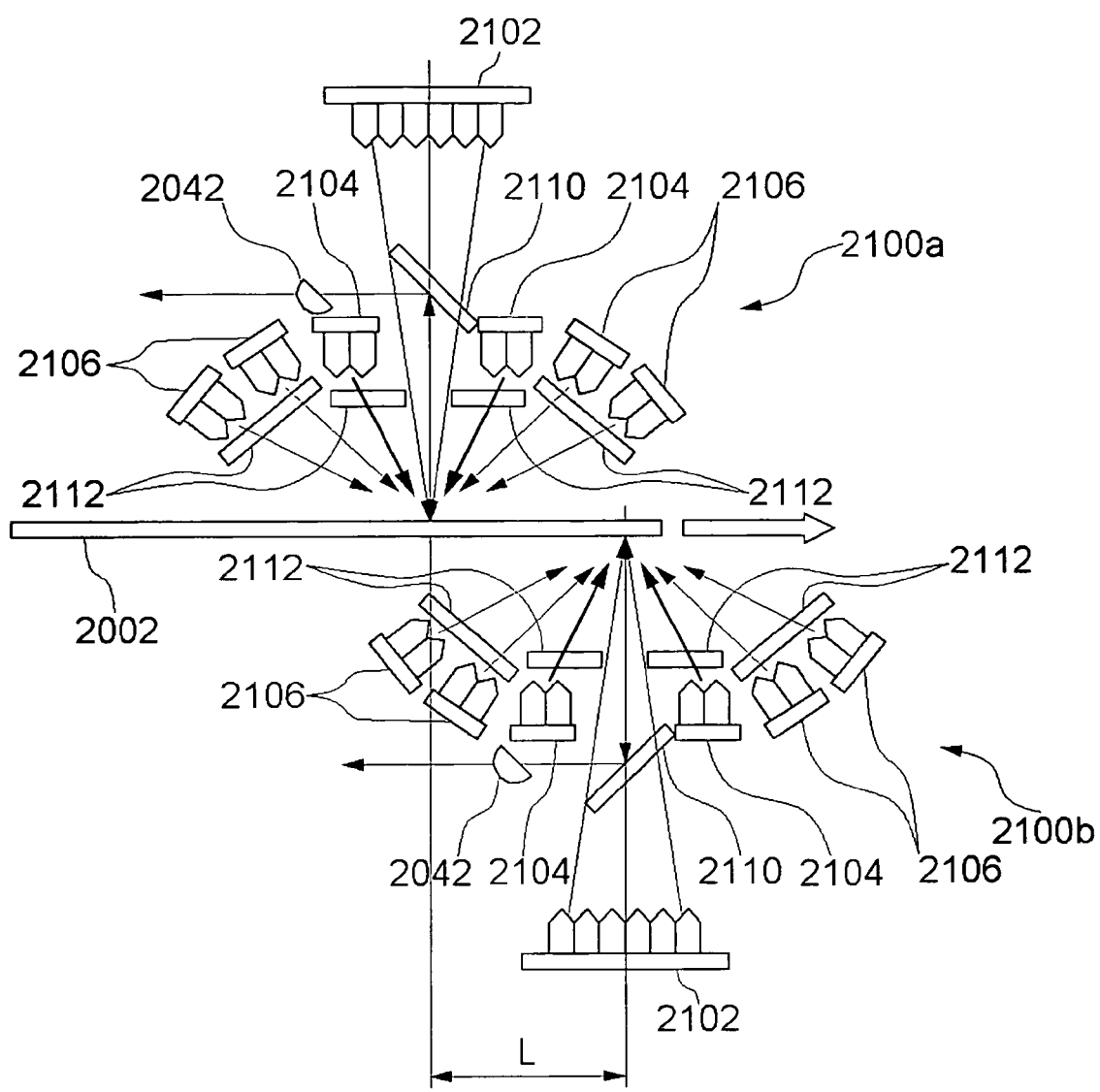
FIG. 17 is a schematic view showing the structure of an illuminating unit included in the imaging unit of FIG. 16.

FIG. 17 is a schematic view showing the structure of the illuminating units 2100 included in the imaging units 2080. The illuminating units 2100 include the front illuminating unit 2100a of the front imaging unit 2080a and the back illuminating unit 2100b of the back imaging unit 2080b. Each of the front illuminating unit 2100a and the back illuminating unit 2100b comprises a first light source 2102, a second light source 2104, a third light source 2106, a half mirror 2110, an acrylic sheet 2112 and the like. The first light source 2102, the second light source 2104 and the third light source 2106 are arranged to surround the half mirror 2110.

The first light source 2102 comprises a group of green light emitting diodes (LEDs) arranged in the scanning direction of the first and second line sensors 2034a and 2034b or the scanning direction of the third and fourth line sensors 2034c and 2034d. The green diodes extend in a length equal to or longer than the width of the board 2002. The first light source 2102 of the front illuminating unit 2100a is provided immediately above a scanned line on the board 2002 scanned by the line sensors 2034a and 2034b of the front imaging unit 2080a for substantially perpendicular incident illumination of the board 2002 below. In contrast, the first light source 2102 of the back illuminating unit 2100b is provided immediately below a scanned line on the board 2002 scanned by the line sensors 2034c and 2034d of the back imaging unit 2080b for substantially perpendicular incident illumination of the board 2002 above.

The angle of incidence of light emitted by the first light source 2102 and incident on the inspected surface of the board 2002 via the half mirror 2110 is substantially zero. In this embodiment, the first light source 2102 is designed to provide a certain beam width, ensuring that some light components are incident on the board 2002 at an angle of incidence of zero, even if the board 2002 is warped. Light reflected from the board 2002 (scanned line) is reflected by the half mirror 2100 and is transmitted through the intermediate lens 2042 before being incident on a set of the first lens 2032a and the second lens 2032b, or a set of the third lens 2032c and the fourth lens 2032d. By using the first light source 2102 for incident illumination of the board 2002 and detecting the light by the line sensors 2034, displacement of components, missing components and solder wetting characteristics on the board 2002 can be determined. For efficient incident illumination of a scanned line, the board populated with the LED group may be divided in the middle into two sub-boards each of which carries a group of LEDs.

The second light source 2104 comprises a group of white light emitting diodes (LEDs) arranged in the scanning direction of the first and second line sensors 2034a and 2034b or the scanning direction of the third and fourth line sensors 2034c and 2034d. The white diodes extend in a length equal to or longer than the width of the board 2002. Each of the illuminating units 2100a and 2100b is provided with two second light sources 2104 which are provided to sandwich a scanned line on the board 2002 in the direction in which the board 2002 is transported so as not to interfere with incident illumination of the scanned line by the first light source 2102.

The third light source 2106 comprises a group of blue LEDs arranged in the scanning direction of the first and second line sensors 2034a and 2034b or the scanning direction of the third and fourth line sensors 2034c and 2034d. The blue diodes extend in a length equal to or longer than the width of the board 2002. Each of the illuminating units 2100a and 2100b is provided with four third light sources 2106 (two on each side) sandwiching a scanned line on the board 2002 in the direction in which the board 2002 is transported so as not to interfere with illumination of the scanned line by the first light source 2102 and the second light source 2104.

As described above, the first light source 2102 emits green light, the second light source 2104 emits white light and the third light source 2106 emits blue light. Thus, each of the illuminating units 2100a and 2100b functions as a composite light source illuminating the board 2002 with multiple colors. A green LED and a blue LED are brighter than a white LED. Accordingly, by designing the first light source 2102 to emit green light and the third light source 2106 to emit blue light, a clear image with a high S/N ratio is obtained. Since a majority of printed boards are green in color, the first light source designed as a source of green light achieves bright incident illumination on the plane. Characters and the like printed by laser on components such as an IC chip or a connector mounted on the board 2002 are properly recognizable by designing the third light source 2106 as a source of blue light and by illuminating the components with blue light at a low angle.

In this embodiment, the acrylic sheet 2112 for diffusing light from the second light source 2104 and the third light source 2106 is provided between the second light source 2104 and a scanned line and between the third light source 2106 and the scanned line. Thus, even when each of the second light source 2104 and the third light source 2106 comprises a set of LEDs as point light sources, the diffusive action minimizes the occurrence of a spot light presenting itself as a reflected image and impairing inspection precision. In this embodiment, the second light source 2104 emitting while light, the first light source 2102 emitting green light and the third light source 2106 emitting blue light are driven independently in the stated order so as to illuminate a scanned line three times. In each illumination, the line sensors 2034 scan the board 2002. In this way, images of the board 2002 as illuminated by the light sources 2102, 2104 and 2106 are obtained.

There may be a hole provided in the board 2002 or a hole may remain incompletely filled with solder. In such a instance, light from one of the illuminating units 2100 may leak to the other of the illuminating units 2100 via the hole. In case light leaked to the other of the illuminating units 2100 is directly scanned by the line sensors 2034, a phenomenon called blooming occurs, which may adversely affect imaging of the board 2002. Therefore, the front illuminating unit 2100a and the back illuminating unit 2100b in this embodiment are provided with an offset of L with respect to each other in the direction in which the board is transported. That is, as seen in FIG. 17, the front illuminating unit 2100a is provided upstream of the back illuminating unit 2100b in the direction in which the board is transported. The offset L may preferably be 50 mm or longer in respect of suppression of blooming.

Figure 18:
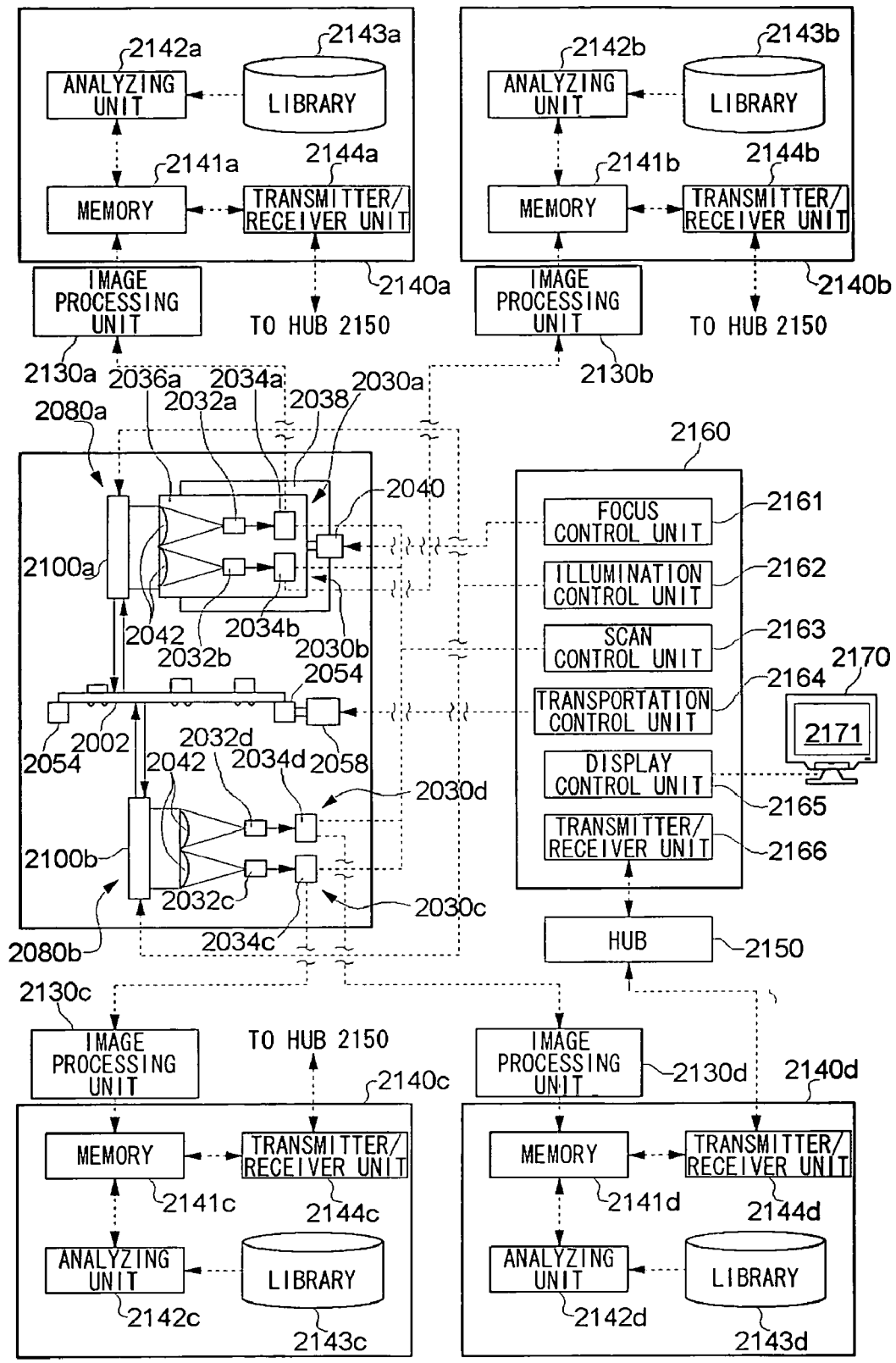
FIG. 18 is a diagram showing a control block in the appearance inspection apparatus according to the third embodiment.

FIG. 18 is a control block diagram of the appearance inspection apparatus 2200. As shown in FIG. 18, the first line sensor 2034a included in the first imaging unit 2030a of the front imaging unit 2080a is connected to a first slave PC 2140a (inspecting unit) via a first image processing unit 2130a. The second line sensor 2034b included in the second imaging unit 2030b of the front imaging unit 2080a is connected to a second slave PC 2140b via a second image processing unit 2130b. The first slave PC 2140a and the second slave PC 2140b function as front surface inspecting units corresponding to the front imaging unit 2080a.

Similarly, the third line sensor 2034c included in the third imaging unit 2030c of the back imaging unit 2080b is connected to a third slave PC 2140c (inspecting unit) via a third image processing unit 2130c. The fourth line sensor 2034d included in the fourth imaging unit 2030d of the back imaging unit 2080b is connected to a fourth slave PC 2140d via a fourth image processing unit 2130d. The third slave PC 2140c and the fourth slave I-C 2140d function as back surface inspecting units corresponding to the back imaging unit 2080b. Hereinafter, the first image processing unit 2130a, the second image processing unit 2130b, the third image processing unit 2130c and the fourth image processing unit 2130d will generically be referred to as image processing units 2130. The first slave PC 2140a, the second slave PC 2140b, the third slave PC 2140c and the fourth slave PC 2140d will generically be referred to as slave PCs 2140. Each of the image processing units 2130 processes an image captured by a corresponding imaging unit 2030 so as to generate image data.

In addition to a CPU, ROM and RAM, the slave PCs 2140a-2140d are respectively provided with memories 2141a-2141d for storing image data and the like transmitted from the image processing units 2130a-2130d, respectively. Analyzing units 2142a-2142d that use the CPU and the like to analyze and inspect the image data stored in the memories 2141a-2141d, respectively, are built in the slave PCs 2140a-2140d, respectively. Further, the slave PCs 2140a-2140d are provided with libraries 2143a-2143d storing inspection data used for analysis by the analyzing units 2142a-2142d as determination criteria for determining whether the board 2002 passes the inspection. The slave PCs 2140a-2140d are also provided with transmitter and receiver units 2144a-2144d for data transmission and reception.

Each of the transmitter and receiver units 2144a-2144d of the slave PCs 2140a-2140d is connected to the other slave PCs via a switching hub 1150 to enable mutual data communication. The slave PCs 2140a-2140d are also connected to a master PC 2160 via the switching hub 2150. In this way, data communication between the master PC 2160 and each of the slave PCs 2140a-2140d is also enabled. The master PC 2160 is provided with a CPU, a ROM, a RAM, a memory and an input/output interface. The master PC 2160 functions as a managing unit for managing the appearance inspection apparatus 2200 as a whole. A focus control unit 2161, an illumination control unit 2162, a scan control unit 2163 and a transport control unit 2164 are built in the master PC 2160 by using a CPU and the like. The master PC 2160 is also provided with a display control unit 2165 and a transmitter and receiver unit 2166 for data transmission and reception. As shown in FIG. 18, the display control unit 2165 controls a display 2170 for displaying a final inspection result, and the transmitter and receiver unit 2166 is connected to the switching hub 2150.

The focus control unit 2161 controls the focusing motor 2040 provided in the front imaging unit 2080a. In this embodiment, the focus control unit 2161, the focusing motor 2040, and the sliding mechanism provided between the front support frame 2036a and the base frame 2038 constitute a focusing mechanism for focusing on the board 2002 without changing an image magnification factor. The illumination control unit 2162 controls the front illuminating unit 2100a and the back illuminating unit 2100b. The scan control unit 2163 controls the scanning of the inspected piece by the first line sensor 2034a and the second line sensor 2034b of the front imaging unit 2080a and by the third line sensor 2034c and the fourth line sensor 2034d of the back imaging unit 2080b. Further, the transport control unit 2164 controls the transport motor 2058. Transportation of the board 2002 set up on the transport rails 2054 (transport belts) and line-by-line movement of the board 2002 are controlled by the transport control unit 2164.

The transmitter and receiver unit 2166 of the master PC 2160 may be connected to the other PCs and the like via a local area network (LAN). In this way, the master PC 2160 is allowed to supply an inspection result to the other PCs and the like. An input/output unit such as a keyboard and a mouse (not shown) is connected to the master PC 2160. A user is capable of performing an operation such as data input to the appearance inspection apparatus 2200 via the keyboard and the like.

A procedure for appearance inspection of an inspection piece by the appearance inspection apparatus 2200 will now be described with reference to FIGS. 19-23.

Figure 19:
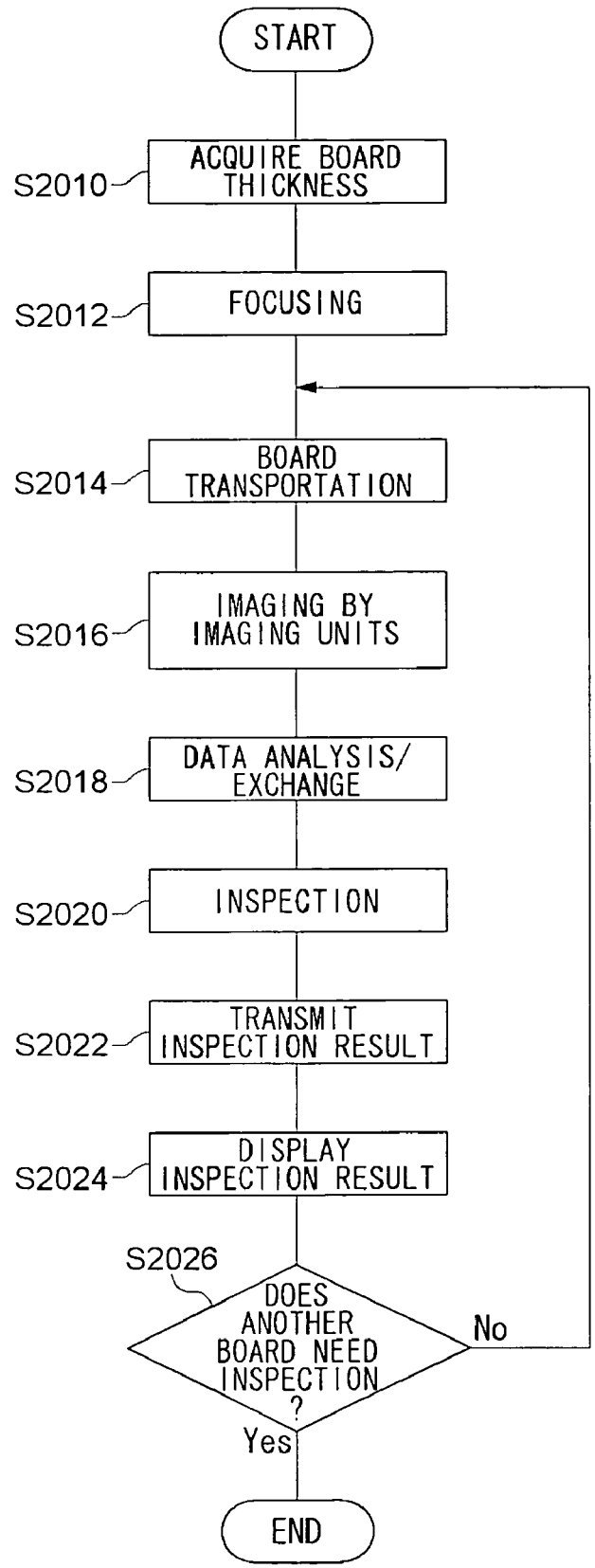
FIG. 19 is a flowchart for explaining about a procedure for appearance inspection of an inspection piece performed by the appearance inspection apparatus according to the third embodiment.

FIG. 19 is a flow chart showing a procedure for appearance inspection of the board 2002 by the appearance inspection apparatus 2200. FIG. 19 shows a procedure for simultaneously inspecting the front surface and the back surface of the board 2002 on which components such as IC chips and connectors are mounted through a reflow process on the front surface of the board and a DIP process on the back surface of the board. As shown in FIG. 19, inspection of the board 2002 is started by the focus control unit 2161 of the master PC 2160 referring to board information (inspection data) input before the inspection so as to acquire information on the thickness of the board 2002 from (S2010). The thickness of the board 2002 may be input to the master PC 2160 by a user by using a keyboard or a mouse. Once the thickness of the board 2002 is acquired, the focus control unit 2161 of the master PC 2160 reads, from a focus control adjustment table stored in a predetermined storage area, the amount of movement (for example, on the order of 0.3-2.0 mm) of the front support frame 2036a with respect to the base frame 2038 proportional to the thickness of the board 2002 input in S2010. The focus control unit 2161 controls the focusing motor 2040 so as to move the front support frame 2036a by the amount thus read (S2012).

As already described, the first and second line sensors 2034a and 2034b, the first and second lenses, the intermediate lens 1042 and the like constituting an imaging system (optical system) of the front imaging unit 2080a are fixed on the front support frame 2036a. Therefore, as a result of the front support frame 2036a being moved with respect to the base frame 2038, the focal distance between the board (inspection piece) and the lens (i.e. a total of a distance x2001 between the end face of the intermediate lens 2042 and the half mirror 2100 and a distance x2002 between the half mirror 2110 and the surface of the board 2002) (see FIG. 16) changes. As a result, focusing on the board 2002 is achieved without changing an image amplification factor. Thus, the appearance inspection apparatus 2200 is provided with a focusing mechanism for varying the focal distance (x2001+x2002) from the board 2002 in accordance with the dimension of the board 2002 in an imaging direction (i.e. in accordance with the thickness of the board 2002). As a result, the appearance inspection apparatus 2200 achieves focusing on the surface of the board 2002 and allows a clear image to be obtained, even if the thickness of the board 2002 varies from board to board. Accordingly, inspection can be performed with high precision.

When the focusing process in S2012 is completed, the transport control unit 2164 of the master PC 2160 causes the board transport table 2050 to start transporting the board 2002 as far as the imaging units 2080 (S2014). As already described, the front illuminating unit 2100a is provided upstream of the back illuminating unit 2100b in the direction in which the board 2002 is transported. Therefore, the board 2002 is initially moved by the board transport table 2050 to a start position within the scanning range of the first line sensor 2034a and the second line sensor 2034b of the front imaging unit 2080a. When the board 2002 is transported as far as a start position within the scanning range of the first line sensor 2034a and the second line sensor 2034b of the front imaging unit 2080a, the illumination control unit 2162 of the master PC 2160 causes the front illuminating unit 2100a and the back illuminating unit 2100b to start illuminating the board 2002. The scan control unit 2163 of the master PC 2160 causes the first and second imaging units 2030a and 2030b of the front imaging unit 2080a and the third and fourth imaging units 2030c and 2030d of the back imaging unit 2080b to start capturing images of the front and back surfaces of the board 2002 (S2016).

When imaging by the imaging units 2080a and 2080b is started in S2016, the first line sensor 2034a, the second line sensor 2034b, the third line sensor 2034c and the fourth line sensor 2034d are controlled by the scan control unit 2163 to synchronously scan the board 2002 in each unit scanning step. When the front surface of the board 2002 is illuminated by the front illuminating unit 2100a with light, the first line sensor 2034a of the first imaging unit 2030a scans the board 2002 through the intermediate lens 2042 and the first lens 2032a. The second line sensor 2034b of the second imaging unit 2030b scans through the intermediate lens 2042 and the second lens 2032b. When the back surface of the board 2002 is illuminated by the back illuminating unit 2100b with light, the third line sensor 2034c of the third imaging unit 2030c scans the board 2002 through the intermediate lens 2042 and the third lens 2032c. The fourth line sensor 2034d of the fourth imaging unit 2030d scans through the intermediate lens 2042 and the fourth lens 2032d. In this way, by using the line sensors 2034a-2034d, the mechanism is simplified and inspection time is reduced as compared with a related-art structure in which an inspected surface is made to travel in two dimensions and then halted, which steps are repeated for successive spot images to be taken.

Each time the board 2002 is scanned one line by the first through fourth line sensors 2034a-2034d, the transport control unit 2164 of the master PC 2160 supplies a control signal to the transport motor 2058 for driving the feed screw 2056 so as to advance the board 2002 by one line. In this way, scanning by the first through fourth line sensors 2034a-2034d can be performed in one sitting. The board 2002 can be moved by the transport control unit 2164 while scanning by the first through fourth line sensors 2034a-2034d is not being performed. Therefore, the board 2002 is scanned efficiently so that inspection time is reduced. A unit scanning step is a unit step of scanning operation each of the line sensors 2034a-2034d is capable of performing. For example, a unit scanning step refers to a one-way scan from one end of the board 2002 to the other or a two-way scan.

By allowing the first through fourth line sensors 2034a-2034d to scan the entire length of the board 2002 in the direction in which the board 2002 is transported, imaging of both surfaces of the board 2002 is completed in a single board transportation process. That is, the board 2002 is transported by the board transport table 2050 between the front imaging unit 2080a and the back imaging unit 2080b. The front imaging unit 2080a captures an image of the front surface of the board 2002 in a single transportation process, and the back imaging unit 2080b captures an image of the back surface of the board 2002 in a single transportation process. The term "single transportation process" may refer to a process whereby the board 2002 is transported in one direction only or a process whereby the board 2002 reciprocates.

In this embodiment, the illumination control unit 2162 controls the front illuminating unit 2100a and the back illuminating unit 2100b so that illumination associated with the execution of each unit scanning step is performed synchronously while images of the board 2002 are being captured by the imaging units 2080a and 2080b. The scan control unit 2163 controls the first through fourth line sensors 2034a-2034d so that scanning of the board 2002 is performed synchronously while the front illuminating unit 2100a and the back illuminating unit 2100b are illuminating the board 002 with light.

More specifically, the illumination control unit 2162 controls the front illuminating unit 2100a and the back illuminating unit 2100b to simultaneously illuminate the board 2002 with light of the same color. In this embodiment, the second light source 2104 emitting while light, the first light source 2102 emitting green light and the third light source 2106 emitting blue light are driven in the stated order so that the front illuminating unit 2100a and the back illuminating unit 2100b illuminate the board 2002 with white light, green light and blue light in the stated order. Therefore, even if light from the front illuminating unit 2100a leaks to the back surface of the board 2002 illuminated by the back illuminating unit 2100b, as a result of a peripheral component presenting itself as a reflected image, adverse effects of optical interference on the inspection result are minimized.

When the second light sources 2104 of the front illuminating unit 2100a and the back illuminating unit 2100b simultaneously illuminate the board 2002 with white light, the scan control unit 2163 of the master PC 2160 causes the line sensors 2034a-2034d to perform a unit scanning step synchronously. When the first light sources 2102 of the front illuminating unit 2100a and the back illuminating unit 2100b simultaneously illuminate the board 2002 with green light, the scan control unit 2163 causes the line sensors 2034a-2034d to perform an additional unit scanning step synchronously. When the third light sources 2106 of the front illuminating unit 2100a and the back illuminating unit 2100b simultaneously illuminate the board 2002 with blue light, the scan control unit 2163 causes the line sensors 2034a-2034d to perform a still additional unit scanning step synchronously.

As the imaging units 2080a and 2080b capture images of the board 2002, the image obtained by the first line sensor 2034a of the first imaging unit 2030a is transmitted to the first image processing unit 2130a, the image obtained by the second line sensor 2034b of the second imaging unit 2030b is transmitted to the second image processing unit 2130b, the image obtained by the third line sensor 2034c of the third imaging unit 2030c is transmitted to the third image processing unit 2130c, and the image obtained by the fourth line sensor 2034d of the fourth imaging unit 2030d is transmitted to the fourth image processing unit 2130d.

Each of the image processing units 2130a-2130d processes the image from a corresponding one of the line sensors 2034a-2034d. The first image processing unit 2130a transmits the processed image to the memory 2141a of the first slave PC 2140a and stores the image therein. The second image processing unit 2130b transmits the processed image to the memory 2141b of the second slave PC 2140b and stores the image therein. Similarly, the third image processing unit 2130c transmits the processed image to the memory 2141c of the third slave PC 2140c and stores the image therein. The fourth image processing unit 2130d transmits the processed image to the memory 2141d of the fourth slave PC 2140d and stores the image therein.

When imaging of the board 2002 by the front imaging unit 2080a and the back imaging unit 2080b is completed, the transport control unit 2164 of the master PC 2160 moves the board transport table 2050 by supplying an instruction signal to the transport motor 2058 and rotating the feed screw 2056 accordingly, so as to carry the board 2002 for which imaging is completed to a subsequent fabrication step.

When the image data of the board 2002 is stored in each of the memories 2141a-2141d of the slave PCs 2140a-2140d, each of the analyzing units 2142a-2142d of the respective slave PCs 2140a-2140d analyzes the image data stored in a corresponding one of the memories 2141a-2141d. Data necessary for inspection of the board 2002 are exchanged between the slave PCs 2140a-2140d (S2018). Data exchanged in S2018 between the slave PCs 2140a-2140d include data to be shared by the slave PCs 2140a-2140d in inspecting the board 2002 (hereinafter, referred to as data for sharing) and images of components captured by the first imaging unit 2030a, the second imaging unit 2030b, the third imaging unit 2030c and the fourth imaging unit 2030d. Data for sharing include data indicating the position of an identification mark on the board 2002 that serves as a reference for positioning, and data such as the serial number and the fabrication date of the board 2002 obtained by analyzing a tag mark such as a bar code provided on the board 2002.

Figure 20A:
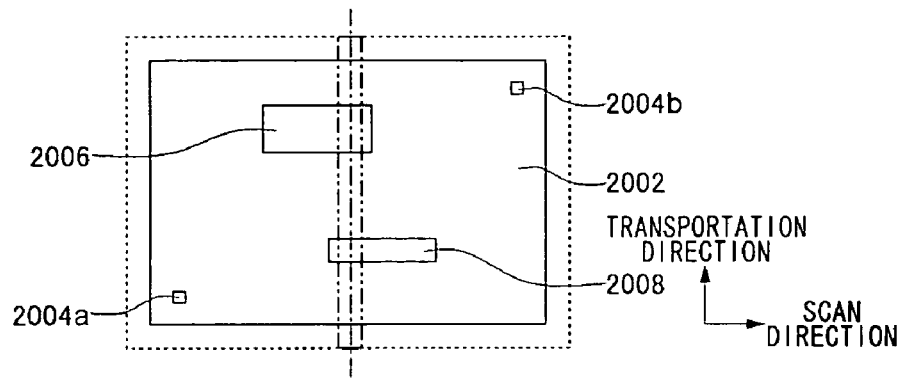
FIG. 20A is a top view showing the surface of a substrate (inspection piece)

A description will now be given of image data analysis/exchange in S2018, with reference to FIGS. 20A-20C. FIG. 20A is a top view showing the surface of the board 2002. The following description concerns analysis of image data of the surface of the board 2002 and sharing of data. As shown in FIG. 201A, the board 2002 is provided with a first identification mark 2004*a* and a second identification mark 2004*b* that serve as references for positioning of the board 2002. Further, a first component 2006 and a second component 2008 are provided substantially at the center of the board 2002 shown in FIG. 20A to extend across the imaging ranges of the first and second imaging units 2030*a* and 2030*b* of the front imaging unit 2080*a*. A bar code (not shown) storing various data is provided in the board 2002.

As shown in FIG. 20A, an image of the left-half area in the board 2002 as illustrated is captured by the first imaging unit 2030*a* and an image of the right-half area is captured by the second imaging unit 2030*b*. Accordingly, an image of the first identification mark 2004*a* of the board 2002 is captured by the first imaging unit 2030*a* and associated image data is stored in the memory 2141*a* of the first slave PC 2140*a*. An image of the second identification mark 2004*b* of the board 2002 is captured by the second imaging unit 2030*b* and associated image data is stored the memory 2141*b* of the second slave PC 2140*b*. This allows the slave PC 2140*a* corresponding to the first imaging unit 2030*a* to acquire position data from the image data of the identification mark, when analyzing the image data stored in the memory 2141*a*. Similarly, the slave PC 2140*b* corresponding to the second imaging unit 2030*b* acquires position data from the image data of the identification mark, when analyzing the image data stored in the memory 2141*b*. The first slave PC 2140*a* transmits the position data derived from the first identification mark 2004*a* to the other slave PCs 2140*b*, 2140*c* and 2140*d* as data for sharing. The second slave PC 2140*b* transmits the position data derived from the second identification mark 2004*b* to the other slave PCs 2140*a*, 2140*c* and 2140*d*.

As a result, it is possible to address a situation in which the board 2002 is slightly inclined on the transport rails 2054, or the board 2002 is slightly displaced with respect to an ideal position in the scan direction or the transportation direction. More specifically, by allowing the position data, derived from the first identification mark 2004*a* and the second identification mark 2004*b* as references for positioning of the board 2002, to be shared by the slave PCs 2140*a*-2140*d*, the slave PCs 2140*a*-2140*d* can have the knowledge of the position and orientation of the board 2002 even if the an identification mark is not included in the imaging range of the corresponding imaging units 2030*a*-2030*d* or if only some of the identification marks are included in the range.

As shown in FIG. 20A, an overlapping imaging range denoted by an alternate long and two short dashes line is provided between the imaging range of the first imaging unit 2030*a* and the imaging range of the second imaging unit 2030*b* so as not to create a range not scanned by either of the first imaging unit 2030*a* and the second imaging unit 2030*b* of the front imaging unit 2080*a*. Similarly, in the back imaging unit 2080*b*, an overlapping imaging range is provided between the imaging range of the third imaging unit 2030*c* and the imaging range of the fourth imaging unit 2030*d*. Taking an example of the front imaging unit 2080*a*, the imaging range of the first imaging unit 2030*a* extends from the left end of the board 2002 as illustrated in FIG. 20B and slightly into the right half thereof beyond the center line lying in the direction of scan of the board 2002. The imaging range of the second imaging unit 2030*b* extends from the right end of the board 2002 as illustrated and slightly into the left half thereof beyond the center line lying in the direction of scan of the board 2002.

Figure 20B:
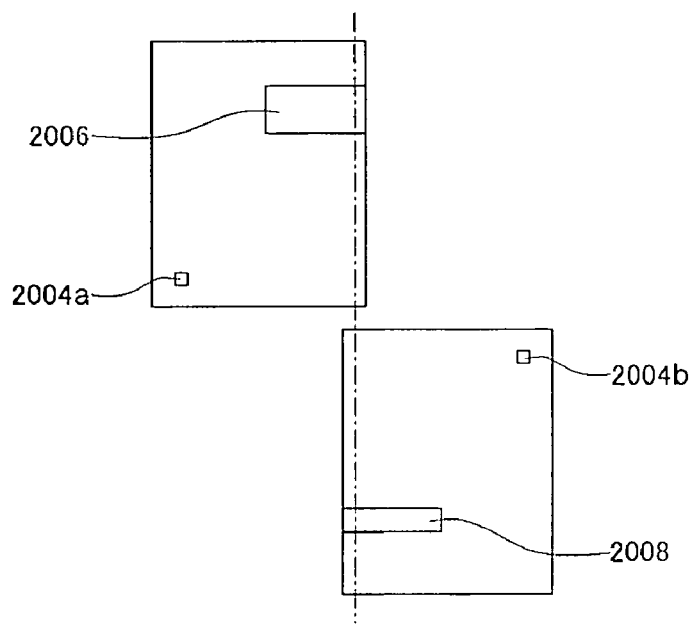
FIG. 20B is a schematic view showing imaging ranges of imaging units.
Figure 20C:
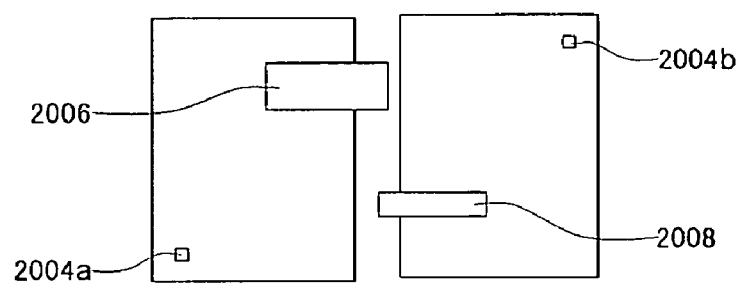
FIG. 20C is a schematic view for explaining about images stored in memories of slave personal computers as inspecting units.

As for components (for example, the first component 2006 and the second component 2008 illustrated in FIGS. 20A-20C) provided on the board 2002 to extend across the imaging ranges of multiple imaging units 2030, the task of inspecting such a component is assigned to a selected one of the slave PCs 2140 corresponding to one of the imaging units 2030 with an imaging range covering the center of the component. For example, as shown in FIG. 20A, the center of the first component 2006 is located within the imaging range of the first imaging unit 2030*a*. Therefore, the first slave PC 2140*a* (inspecting unit associated with the first imaging unit 2030*a*) is responsible for inspecting the first component 2006. Conversely, the second component 2008 is located with the imaging range of the second imaging unit 2030*b*. Therefore, the second slave PC 2140*b* (inspecting unit associated with the second imaging unit 2030*b*) is responsible for inspecting the second component 2008.

In this case, as shown in FIG. 20B, the slave PC 2140*a* does not hold the entirety of the image data of the first component 2006 subject to its inspection, at a point of time when the first image processing unit 2130*a* corresponding to the first imaging unit 2030*a* stores the image data in the memory 2141*a* of the slave PC 2140*a*. Similarly, the slave PC 2140*b* does not hold the entirety of the image data of the second component 2008 subject to its inspection, at a point of time when the second image processing unit 2130*b* corresponding to the second imaging unit 2030*b* stores the image data in the memory 2141*b* of the slave PC 2140*b*.

Thus, each of the slave PCs 2140*a*-2140*d*, upon recognizing image data of a component not subject to its inspection while analyzing image data, transmits the recognized image data to one of the slave PCs 2140*a*-2140*d* responsible for the inspection of that component (or to other slave PCs 2140*a*-2140*d*). That is, in the example of FIGS. 20A-20C, the memory 2141*a* of the first slave PC 2140*a* includes a portion of the image data of the second component 2008. The image data of the second component 2008 is transmitted from the first slave PC 2140*a* to the second slave PC 2140*b* responsible for the inspection of the second component 2008. The second slave PC 2140*b* stores the image data thus transmitted in the memory 2141*b*. Similarly, the memory 2141*b* of the second slave PC 2140*b* includes a portion of the image data of the first component 2006. The image data of the first component 2006 is transmitted from the second slave PC 2140*b* to the first slave PC 2140*a* responsible for the inspection of the first component 2006. The first slave PC 2140*a* stores the image data thus transmitted in the memory 2141*a*. Thus, as shown in FIG. 20C, each of the slave PCs 2140*a* and 2140*b* can acquire missing image data of a component subject to the PC's inspection.

When analysis/exchange of image data is completed, the analyzing units 2142*a*-2142*d* of the slave PCs 2140*a*-2140*d* perform inspection of respective areas on the board 2002 for which they are responsible, using inspection data stored in the libraries 2143*a*-2143*d* (S2020). In the appearance inspection apparatus 2200, there are provided multiple sets of inspection data which serve as references for determination as to whether a board passes the inspection, for individual components mounted on the board 2002 such as IC chips and connectors, as well as for respective imaging directions of the front imaging unit 2080*a* and the back imaging unit 2080*b*.

In the related-art appearance inspection apparatus, it is general that the front and back surface of the board are not simultaneously inspected. Therefore, the apparatus need not identify a soldering type such as reflow, DIP soldering or hand soldering in accordance with the direction of imaging by the imaging units. In contrast, the appearance inspection apparatus 2200 according to this embodiment is provided with at least one of front inspection data and back inspection data for each component mounted on the board 2002 so as to enable simultaneous inspection of both surfaces of the board 2002.

The front inspection data and the back inspection data each comprises image data and numerical data specifying a solder configuration and the like that pass the inspection. Each inspection data includes an identifier for identifying a soldering type such as reflow, DIP soldering or hand soldering commensurate with the configuration of a solder pad corresponding to a component.

The front inspection data for each component is stored in the library 2142a or the library 2143b provided in the slave PC 2140a or the slave PC 2140b (both of which correspond to the front imaging unit 2080a), respectively which is responsible for the inspection of the component. The back inspection data for each component is stored in the library 2143c or the library 2143d provided in the slave PC 2140c or the slave PC 2140d (both of which correspond to the back imaging unit 2080b), respectively, which is responsible for the inspection of the component. The front inspection data stored in the libraries 2142a and 2143b of the slave PCs 2140a and 2140b responsible for the inspection of the front surface of the board 2002 may be identical to each other. Similarly, the back inspection data stored in the libraries 2143c and 2143d of the slave PCs 2140c and 2140d responsible for the inspection of the back surface of the board 2002 may be identical to each other.

By using the front inspection data and back inspection data in combination with the image data of the board 2002 obtained by using the front imaging unit 2080a and the back imaging unit 2080b in the appearance inspection apparatus 2200, it is possible to scan the board 2002, which is provided with a reflow surface on the front and a DIP surface on the back, in multiple directions (i.e. from above and from below) with high precision. The front inspection data and back inspection data may be individually input to the libraries 2143a-2143d of the slave PCs 2140a-2140d. Alternatively, the entirety of front inspection data and back inspection data may be input to the master PC 2160 in one sitting so that the slave PCs 2140a-2140d acquire the necessary inspection data from the master PC 2160.

In this way, the slave PCs 2140a-2140d of the appearance inspection apparatus 2200 analyze the image data stored in the memories 2141a-2141d and share the resultant data that include an identification mark, bar code, and other data necessary for inspection. The slave PCs 2140a-2140d also exchange the image data necessary for inspection. The slave PCs 2140a-2140d perform the inspection of the board 2002 by using the data for sharing, the image data and the inspection data stored in the libraries 2143a-2143d.

The operation of the slave PCs 2140a-2140d described above is analogous to the workings of a cell inside a living organism. The cells have identical genes and select only those instructions related to them for execution, in accordance with a trigger. Analogy can be drawn between this and the third embodiment in that the data for sharing corresponds to genes and the slave PCs 2140a-2140d correspond to cells. In this embodiment, instead of the master PC 2160 assigning inspection locations and inspection menus to the slave PCs 2140a-2140d and directing the PCs accordingly, the slave PCs 2140 autonomously process image data and perform inspection. As a result, it is possible in the appearance inspection apparatus 2200 to improve precision with which the board 2002 is inspected and reduce inspection time, by allowing the multiple slave PCs 2140a-2140d to share the workload of inspecting the board 2002.

When the inspection in S2020 is completed, each of the slave PCs 2140a-2140d transmits data indicating a result of inspection to the other slave PCs 2140 and the master PC 2160 so as to share the result of inspection with each other (S2022) The data for sharing such as position data stored in the memories 2141a-2141d of the slave PCs 2140a-2140d and derived from identification marks are also transmitted to the master PC 2160. In accordance with an instruction from the CPU, the display controller 2165 of the master PC 2160 causes the result of inspection of the board 2002 on a screen 2171 of a display 2171, by referring to preset CAD data of the board 2002 and the data received from the slave PCs 2140a-2140d (S2024).

Figure 21:
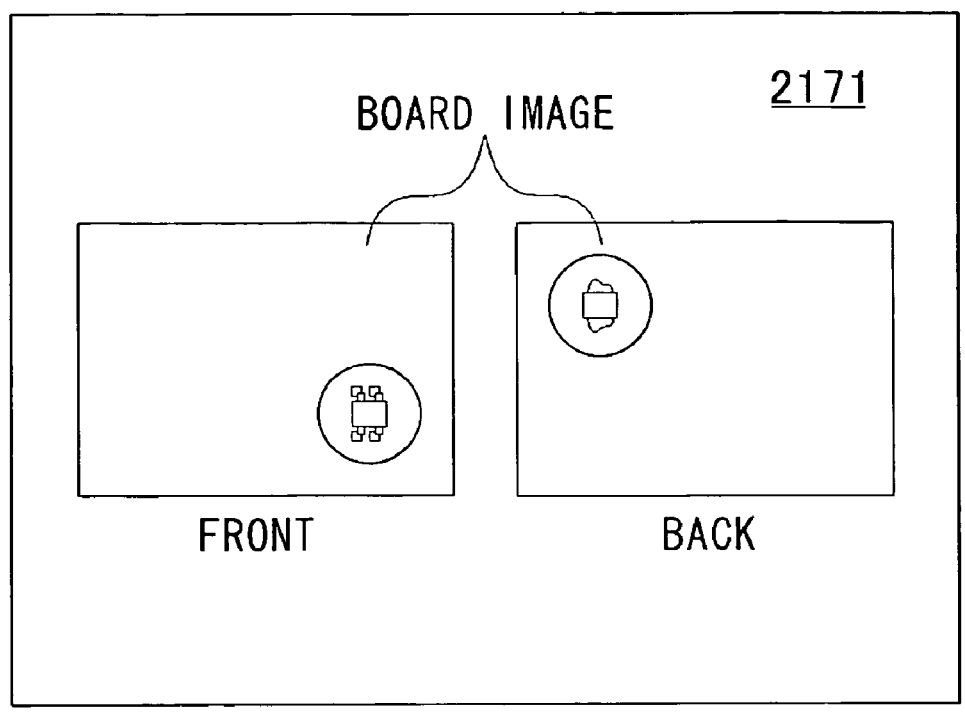
FIG. 21 is a schematic view showing results of inspection displayed on a display included in the appearance inspection apparatus of FIG. 15.

FIG. 21 is a schematic view showing an inspection result displayed on the screen 2171 of the display 2170. As shown in FIG. 21, the display control unit 2165 of the appearance inspection apparatus 2200 according to this embodiment causes the result of inspection of the front surface of the board 2002 and the result of the inspection of the back surface of the board 2002 to be displayed on the screen 2171 of the display 2170 simultaneously. As shown in FIG. 21, the display control unit 2165 also causes the inspection result to be displayed on the screen 2171 such that locations (components) identified by the slave PCs 2140a-2140d to contain a failure are displayed in a manner clearly distinguishable from locations that pass the inspection. In this way, a user can gain the knowledge of the inspection result of both the front surface of an inspection piece and the back surface thereof without mouse operation or the like. Thus, it will be appreciated that the appearance inspection apparatus 2200 presents to a user the inspection result of both the front surface of the board 2002 and the back surface thereof simultaneously, after both surfaces of the board 2002 have been efficiently inspected. Accordingly, usability for users is significantly improved.

Figure 22:
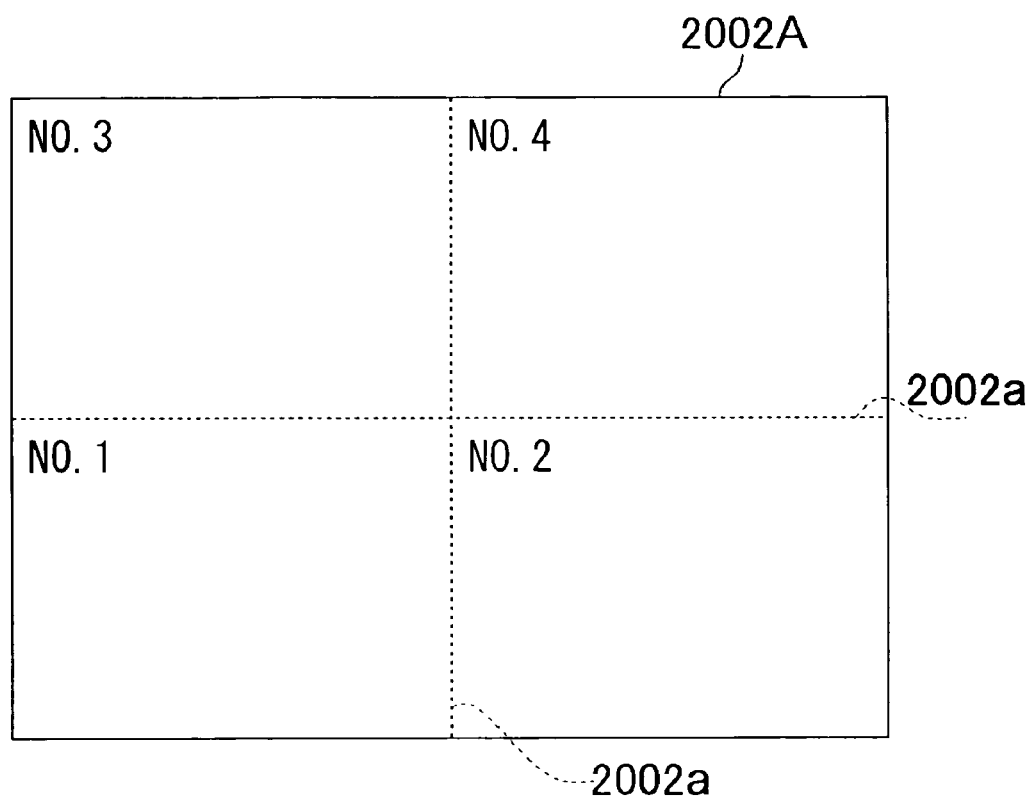
FIG. 22 is a schematic view showing an inspection piece subject to inspection by the appearance inspection apparatus of FIG. 15.
Figure 23:
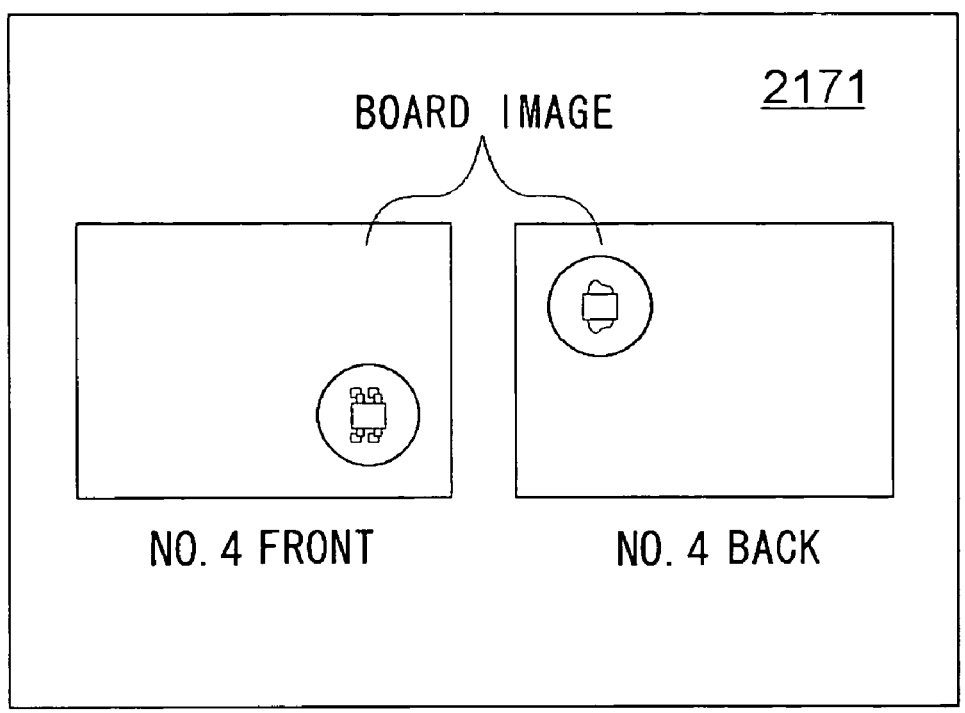
FIG. 23 is a schematic view showing results of inspection displayed on the display included in the appearance inspection apparatus of FIG. 15.

In case the inspection piece is a board 2002A of a type provided with perforations, V notches 2002a or the like as illustrated in FIG. 22 so as to be severed after components have been mounted, the result of inspection by the slave PCs 2140a-2140d may be displayed on the screen 2171 of the display 2170 in a manner illustrated in FIG. 23. That is, if, as a result of inspection by the slave PCs 2140a-2140d of the board 2002A severed as shown in FIG. 22 into four areas No. 2001-No. 2004 after components have been mounted, defects are found in both surfaces of area No. 2004, the display control unit 2165 of the master PC 2160 only causes the front and back surfaces of area No. 2004 containing defects to be displayed on the screen 2171 of the display 2170. By allowing only the front and back surfaces of a selected area in the board 2002A determined to contain a defect as a result of inspection by the slave PCs 2140a-2140d to be displayed on the display 2170, usability for users is significantly improved.

When the result of inspection by the slave PCs 2140a-2140d has been displayed on the display 2170, the master PC 2160 determines whether a similar inspection piece needs inspection (S2026). If it is determined that there is a similar inspection piece, i.e. if it is determined that the board 2002 having the same thickness as the board 2002 for which inspection is completed needs inspection (Yes in S2026), the master PC 2160 causes steps in S2014-S2024 to be performed again. If it is determined that there is not a similar inspection piece (No in S2026), the master PC 2160 terminates inspection by the appearance inspection apparatus 2200.

It is to be understood that the embodiment is not limited by the preferred example as described above. It is also within the scope of the embodiment to make various modifications and changes on the basis of the knowledge of those skilled in the art. Some examples of such modifications will be described below.

Instead of scanning the board 2002 by the line sensors 2034a-2034d, the imaging units 2030a-2030d may capture images of selected ranges successively by using a CCD sensor or the like. According to this modification, images of the board 2002 can be captured equally easily.

Only one imaging unit 2030 and one associated slave PC 2140 may be provided to face the front surface of the board 2002, i.e. above the board 2002, and one each may be provided to face the back surface of the board 2002, i.e. below the board 2002. According to this modification, the number of imaging units 2030 and slave PCs 2140 is reduced so that the cost is curtailed accordingly. In this case, the data for sharing is exchanged between the slave PC 2140 for inspecting the front surface of the board 2002 and the slave PC 2140 for inspecting the back surface. Consequently, provision of an identification mark on one of the surfaces of the board 2002 may be omitted. Inspection is still enabled by using positional data derived from an identification mark on the other surface. As a result, the structure of the board 2002 is simplified.

The imaging unit 2080 including the illuminating units 2100 and the imaging units 2030 may be moved, while the board 2002 is fixed. According to this modification, relative movement of the imaging unit 2080 and the board 2002 is achieved while the board 2002 is maintained in a stable state for imaging of the board 2002.

The data for sharing may be transmitted from the master PC 2160 to the slave PCs 2140 after the slave PCs 2140 transmitted the same to the master PC 2160. In this way, the slave PCs 2140 and the master PC 2160 can share the data easily.

In the embodiment described above, only the front imaging unit 2080a is provided with a focusing mechanism. Alternatively, both the front imaging unit 2080a and the back imaging unit 2080b may be provided with a focusing mechanism depending on the configuration of an inspection piece.

Although a procedure for inspecting both surfaces of the board 2002 simultaneously is described above, the result of inspection of the front surface of the inspection piece and the result of inspection of the back surface of the inspection piece may be acquired through different steps and displayed simultaneously. One of the result of inspection of the front surface and the result of inspection of the back surface may be acquired in another appearance inspection apparatus.

In the embodiment described above, it is assumed that a user inputs the thickness of the board necessary for focusing. Alternatively, the bar code on the board may contain information on the thickness of the board so that focusing is performed when an image of the bar code has been captured and analyzed.

Needless to say, the appearance inspection apparatus according to this embodiment can be used for pre-reflow inspection.

While the preferred embodiments of the present invention have been described using specific terms, such description is for illustrative purposes only, and it is to be understood that changes and variations may be made without departing from the spirit or scope of the appended claims.

What is claimed is:

1. An appearance inspection apparatus which inspects an electronic board comprising:

a first scanning unit which scans a first surface of the electronic board by being moved relative to the electronic board;

a second scanning unit which is provided opposite to the first scanning unit, sandwiching the electronic board, and which scans a second surface of the electronic board by being moved relative to the electronic board; and a moving unit which moves the first scanning unit, the second scanning unit and the electronic board relative to each other, a first illuminating unit which illuminates the electronic board in order for the first scanning unit to scan the electronic board; and a second illuminating unit which illuminates the electronic board in order for the second scanning unit to scan the electronic board, wherein the first illuminating unit and the second illuminating unit synchronously illuminate the electronic board in association with each scanning unit illuminating different locations offset from each other in a direction of relative movement of the electronic board with respect to the first and second scanning units.

2. The appearance inspection apparatus according to claim 1, wherein the first illuminating unit and the second illuminating unit each comprises a composite light source illuminating the electronic board at multiple angles of incidence, and the first illuminating unit and the second illuminating unit illuminate the electronic board at the same angle of incidence at the same time for synchronous illumination.

3. The appearance inspection apparatus according to claim 1, further comprising a support member on which the second surface of the electronic board is placed, wherein
the first scanning unit comprises a focusing mechanism for focusing on the first surface in accordance with the thickness of the electronic board, without changing an image magnification factor.

4. The appearance inspection apparatus according to claim 1, further comprising:

a first inspecting unit which inspects the first surface by referring to image data obtained by scanning the board with the first scanning unit;

a second inspecting unit which inspects the second surface by referring to image data obtained by scanning the board with the second scanning unit; and a display control unit which receives a result of inspecting the first surface from the first inspecting unit and also receives a result of inspecting the second surface from the second inspecting unit, and which causes the result of inspecting the first and second surfaces thus received to be simultaneously displayed on a display.

5. The appearance inspection apparatus according to claim 1, wherein each of the first and second illuminating units illuminates the board with multiple colors successively such that the units synchronously illuminate the electronic board with the same color.

* * * * *

UNITED STATES PATENT AND TRADEMARK OFFICE
CERTIFICATE OF CORRECTION

PATENT NO. : 7,590,279 B2  Page 1 of 1
APPLICATION NO. : 11/314092
DATED : September 15, 2009
INVENTOR(S) : Yoshihiro Akiyama It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 935 days.

Signed and Sealed this

Twenty-first Day of September, 2010

David J. Kappos
*Director of the United States Patent and Trademark Office*